(12) United States Patent
Tredwell et al.

(10) Patent No.: US 8,866,099 B2
(45) Date of Patent: Oct. 21, 2014

(54) RADIOGRAPHIC DETECTOR ARRAYS INCLUDING SCINTILLATORS AND METHODS FOR SAME

(71) Applicants: Timothy J. Tredwell, Fairport, NY (US); Gregory N. Heiler, Hilton, NY (US)

(72) Inventors: Timothy J. Tredwell, Fairport, NY (US); Gregory N. Heiler, Hilton, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/798,244

(22) Filed: Mar. 13, 2013

(65) Prior Publication Data

US 2013/0221230 A1 Aug. 29, 2013

Related U.S. Application Data

(63) Continuation of application No. 13/805,423, filed as application No. PCT/US2012/026839 on Feb. 28, 2012.

(51) Int. Cl.
*H01L 27/146* (2006.01)
*H01L 31/18* (2006.01)
*G01T 1/20* (2006.01)

(52) U.S. Cl.
CPC . *G01T 1/20* (2013.01); *H01L 31/18* (2013.01); *H01L 27/146* (2013.01); *H01L 27/14663* (2013.01)
USPC .................................................. 250/370.11

(58) Field of Classification Search
CPC ................................................ H01L 27/14663
USPC ................................................... 250/370.11
See application file for complete search history.

(56) References Cited

U.S. PATENT DOCUMENTS

| | | | |
|---|---|---|---|
| 3,940,626 A | 2/1976 | Hounsfield | |
| 5,506,409 A | 4/1996 | Yoshida et al. | |
| 5,517,031 A * | 5/1996 | Wei et al. | 250/370.08 |
| 6,348,693 B1 * | 2/2002 | Weisfield et al. | 250/370.11 |
| 6,462,344 B1 * | 10/2002 | Joo et al. | 250/370.09 |
| 6,469,305 B2 | 10/2002 | Takabayashi et al. | |
| 6,608,312 B1 | 8/2003 | Okada et al. | |
| 6,770,885 B2 | 8/2004 | Eberhard et al. | |
| 2003/0226974 A1 * | 12/2003 | Nomura et al. | 250/370.11 |
| 2004/0262536 A1 | 12/2004 | Van den Bergh et al. | |
| 2005/0002490 A1 | 1/2005 | Bergh et al. | |
| 2008/0099687 A1 | 5/2008 | Shoji et al. | |
| 2008/0302970 A1 * | 12/2008 | Fujieda et al. | 250/370.11 |
| 2013/0048960 A1 * | 2/2013 | Nishino et al. | 257/40 |

FOREIGN PATENT DOCUMENTS

| | | | |
|---|---|---|---|
| JP | 2002-055165 | | 2/2002 |
| JP | 2010019620 A | * | 1/2010 |

OTHER PUBLICATIONS

Machine (Google) translation of JP 2010-19620 A.*
International Search Report mailed Jul. 31, 2012 for PCT International Application No. PCT/US2012/026839, 2 pages.

* cited by examiner

*Primary Examiner* — Constantine Hannaher

(57) ABSTRACT

A projection radiographic imaging apparatus includes an imaging array with imaging pixels formed over an insulating substrate. A scintillator converts radiographic radiation to photoelectric radiation proximate to the imaging array. A dielectric layer disposed between the scintillator and the imaging array has a dielectric constant less than 3.0. A continuous or patterned anti-static layer disposed between the imaging array and the scintillator is connected to one or more conductive traces in the imaging array.

19 Claims, 30 Drawing Sheets

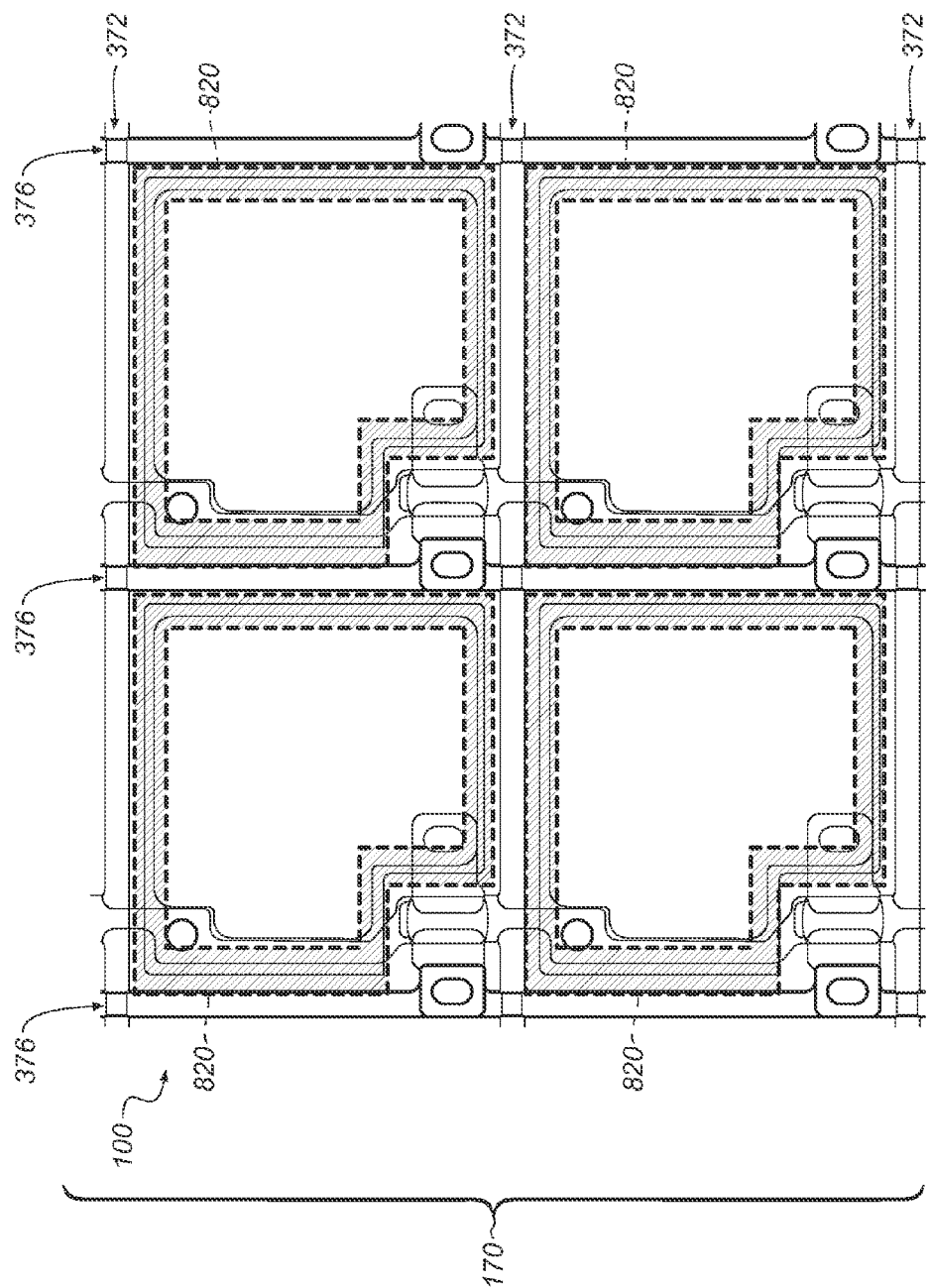

RADIOGRAPHIC DETECTOR ARRAYS INCLUDING SCINTILLATORS AND METHODS FOR SAME

CROSS REFERENCE TO RELATED APPLICATIONS

This is a Continuation of U.S. Ser. No. 13/805,423 entitled DIGITAL RADIOGRAPHIC IMAGING ARRAYS INCLUDING PATTERNED ANTI-STATIC PROTECTIVE COATING WITH SYSTEMS AND METHODS FOR USING THE SAME, to Timothy J. Tredwell, which is a U.S. national stage application of International Application No. PCT/US2012/026839 filed on Feb. 28, 2012.

TECHNICAL FIELD

The present application relates to radiographic imaging arrays. More specifically, the present application relates to indirect digital radiographic imaging arrays and methods for using the same.

DESCRIPTION OF RELATED ART

An indirect digital radiographic (DR) detector can include a scintillator (e.g., phosphor scintillating screen) arranged in proximity to an imaging array sensitive to radiation emitted by the scintillator upon absorption of X-rays or the like. In order to maintain high resolution, the scintillating screen can be mounted in contact with the imaging array or within about 20 microns of a surface of the imaging array. Greater spacing between the imaging array and the scintillator can result in a loss of resolution. For example, this loss of resolution can occur because of multiple reflections of light between the scintillator and the active surface of the imaging array. In addition, greater spacing or non-uniform spacing can result in image non-uniformity because of non-uniformity in optical coupling between the scintillator and the imaging array.

Digital radiographic imaging arrays have been used in radiographic settings in which a readiographic detector is mounted inside a Potter-Bucky grid ("bucky"), mounted at a positioning arm or moved from one location to another (e.g., portable DR detectors). Portability can increase an opportunity for a detector to be dropped or subjected to shock/vibration. In addition, for some portable imaging procedures, the patient stands or lies on the detector, which can result in localized regions of high pressure.

Scintillators can be deposited to (e.g., vacuum evaporation, coating) or attached to an imaging array. Two approaches have been used in the related art to attach a scintillator to an imaging array. In the first, the scintillator can be placed in physical contact with the imaging array using pressure between the non-active surface (e.g., substrate) of the imaging array and a substrate of the scintillator. The second approach uses one or more intermediary layers between the imaging array and the scintillator, for example, a planarization layer, an optical matching layer, an adhesive layer, etc., to attach the scintillator to the imaging array in the detector.

The first approach can have various disadvantages. For example: 1) non-uniform optical contact between the scintillator and photosensing elements; 2) mechanical grinding; 3) lateral scattering of light because of reflections off the active surface of the imaging array and the surface of the scintillator facing the active surface of the imaging array can result in loss of resolution; 4) changing size of an air gap because a surface of the scintillator facing the active surface of the imaging array can include surface roughness on the order of several microns and/or 5) change in position of the scintillator. Since the imaging array and scintillator can be calibrated for pixel-by-pixel gain, a change in position can result in photosensitivity pattern noise because of the calibration no longer being accurate. Also, poor optical coupling of the light from the scintillator to the imaging array can result from optical index matching of an air gap (n=1) formed between the scintillator and the imaging array. Further, changes in the optical coupling of the scintillator to the imaging array can occur when pressure (e.g., localized) is placed on the scintillator resulting in localized hot spots since gain calibration is obtained without pressure.

Examples of the second approach can include a planarization layer as taught, for example, in US20080099687A1 (Konica), U.S. Pat. No. 6,608,312B1 (Canon), and U.S. Pat. No. 6,770,885B2 (GE), all of which are herein incorporated by reference in their entirety. A liquid index matching material as taught by, e.g., U.S. Pat. No. 6,469,305B2 (Hamamatsu) also herein incorporated by reference in its entirety. Such arranged layers can improve the optical coupling of the light between the scintillator and the imaging array and can reduce the impact of localized pressure on the scintillator. U.S. Pat. No. 5,506,409A (Hitachi) discloses detector arrays using spacing beads to maintain a precise separation distance between the scintillator and the imaging array, which is also herein incorporated by reference in its entirety.

SUMMARY

Accordingly, it is an aspect of this application to address in whole or in part, at least the foregoing and other deficiencies in the related art.

It is another aspect of this application to provide in whole or in part, at least advantages described herein.

Another aspect of the application is to provide in whole or in part radiographic detector imaging arrays including high performance imaging characteristics that include imaging arrays.

Another aspect of the application is to provide in whole or in part detector imaging arrays with scintillators (e.g., scintillating phosphor screens) combined with imaging arrays. For example, detector arrays can include a layer between a scintillator and an imaging array to control noise or reduce noise for the imaging array. For example, the layer can include a low dielectric constant layer and/or an anti-static layer.

Another aspect of the application is to provide detector imaging arrays with scintillators combined with imaging arrays using two or more intermediate layers. For example, a detector can include scintillators mounted to imaging arrays using two or more low dielectric constant layers. For example, a first low dielectric constant layer can be transparent and a second low dielectric constant layer can include non-transparent or opaque materials (e.g., colorants). For example, a second low dielectric constant layer can be at non-active locations for an active surface of the imaging array. Alternatively, a first insulating layer can be thick and a second insulating layer can be thin.

Another aspect of the application is to provide detector imaging arrays with scintillating phosphor screens mounted to imaging arrays using at least one intermediate layer such as a low dielectric constant therebetween where additional layers can be added between the scintillator and the imaging array, including planarization layers, adhesive layers, optical matching layers, protective layers, etc.

Another aspect of the application is to provide detector imaging arrays with scintillating phosphor screens combined with or proximate to imaging arrays using at least one intermediate layer such as a antistatic layer therebetween where additional layers can be added between the scintillator and the imaging array, including planarization layers, adhesive layers, optical matching layers, protective layers, etc.

Another aspect of the application is to provide detector imaging arrays using at least one antistatic layer thereover. Another aspect of the application is to provide detector imaging arrays with scintillating phosphor screens combined with imaging arrays using at least one antistatic layer therebetween. Exemplary antistatic layers can be electrically coupled to conductive traces within the radiographic imaging array or within/adjacent imaging pixels of the radiographic imaging array.

Another aspect of the application is to provide detector imaging arrays using at least one patterned antistatic layer thereover. A patterned antistatic layer can be electrically coupled to conductive traces within the radiographic imaging array or within/adjacent imaging pixels of the radiographic imaging array. For example, the antistat layer can include a colorant material.

In accordance with one embodiment, there can be provided a projection radiographic imaging apparatus, that can include an insulating substrate; an imaging array formed over the insulating substrate, the imaging array including imaging pixels, each pixel including at least one readout element and one photosensor; a scintillator to convert first radiographic radiation of one or multiple wavelengths range to second different photoelectric radiation of one or multiple wavelengths range proximate to the imaging array; and a first dielectric layer formed between the scintillator and the imaging array, wherein the dielectric constant of the first dielectric layer is less than 3.0.

In accordance with one embodiment, there can be provided a method of manufacturing a radiographic detector imaging apparatus that can include forming an insulating substrate; forming an imaging array formed over a substrate, the imaging array including imaging pixels, each pixel including at least one readout element and one photosensor, where the photosensor is a polycrystalline photosensor or an amorphous photosensor; forming a scintillator to convert first radiographic radiation of one or multiple wavelengths range to second different photoelectric radiation of one or multiple wavelengths range proximate to the imaging array; and forming a first insulating layer comprising organic material between the scintillator and the imaging array, where a dielectric constant of the first insulating layer is less than 3.3.

In accordance with one embodiment, there can be provided a projection radiographic imaging apparatus that can include a scintillator; an imaging array formed over a substrate, the imaging array including imaging pixels, each imaging pixel including at least one readout element and one photosensor, where the photosensor is a polycrystalline photosensor or an amorphous photosensor; and a first insulating layer and a second insulating layer formed between the scintillator and the imaging array, where a dielectric constant of the second insulating layer over at least some not photosensitive portions of the imaging array is less than 3.3.

Such aspects are given only by way of illustrative example, and such aspects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

Various features of the embodiments can be more fully appreciated as the same become better understood with reference to the following detailed description of the embodiments when considered in connection with the accompanying figures, in which:

FIG. 28 is a diagram that shows a top-down view of a layout for a patterned anti-static coating shown in FIG. 27.

FIG. 29A is a photo-micrograph of a pixel without TFT light shield and FIG. 29B is a photo-micrograph of the pixel with an overlay of anti-static coating containing colorant material.

DESCRIPTION OF EXEMPLARY EMBODIMENTS

Reference will now be made in detail to nonlimiting exemplary embodiments of the invention, examples of which can be illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments by which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

For simplicity and illustrative purposes, exemplary principles of the invention are described by referring mainly to exemplary embodiments herein. Moreover, in the following detailed description, references are made to the accompanying FIGS. 1-11 and 13-29B, which illustrate specific embodiments. Electrical, mechanical, logical and structural changes can be made to the embodiments without departing from the spirit and scope of the present invention. Descriptions herein are, therefore, not to be taken in a limiting sense and the scope of the application is defined by the appended claims and their equivalents.

Certain embodiments according to the application include radiographic detector arrays including at least one insulator (e.g., a first insulating layer) between a scintillator and an imaging array (e.g., photosensor) where a dielectric constant of the insulator is low. For example, embodiments of an insulating layer can include a dielectric constant less than 3.3, less than 3.0, less than 2.6, less than 2.4, etc. Embodiments of radiographic detector arrays can further include a second insulator (e.g., second insulating layer or a second low dielectric constant layer) formed over at least a portion (e.g., the non-photosensitive regions) of the imaging array. For example, embodiments of a second low dielectric constant insulating layer can be substantially opaque (e.g., to visible light or wavelengths between 450 nm and 650 nm). Embodiments of radiographic detector arrays can further include a third layer that can be electrically conductive over at least a portion of a second insulator and the first insulator. In one embodiment, only a low dielectric constant insulating layer over non-photosensitive regions of the imaging array can be used.

Exemplary embodiments according to the application are shown in FIG. 1 through 11 and 13 through 29B.

Figure 1:
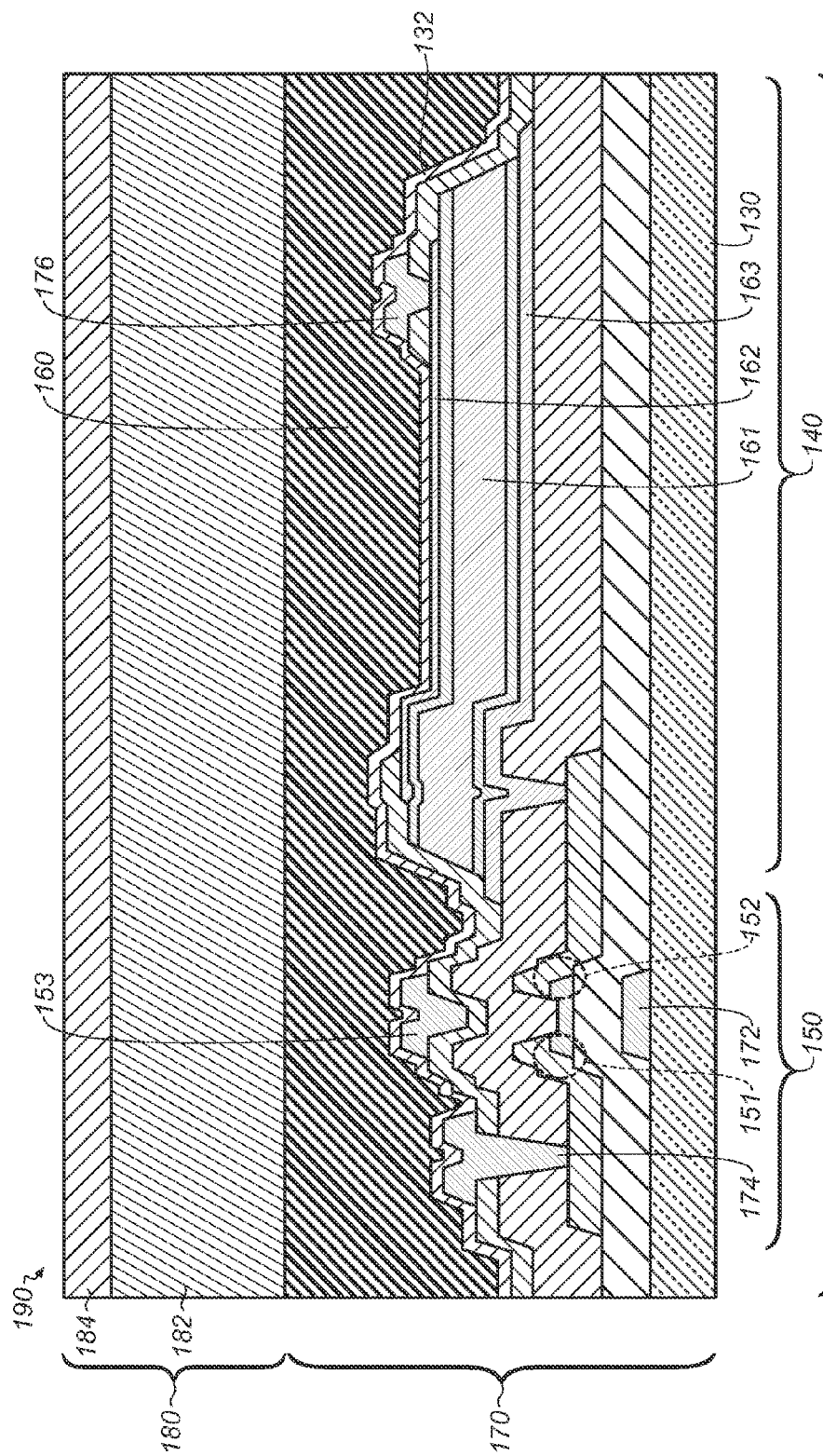
FIG. 1 is a diagram that shows a cross-section of an embodiment of a radiographic detector configured to include a combined scintillator and imaging array according to the application.

FIG. 1 is a diagram that shows a cross-section of an embodiment of a radiographic detector configured to include a combined scintillator and imaging array using a low dielectric constant material in between. As shown in FIG. 1, a detector array can include a low dielectric constant encapsulation (e.g., single layer) of an imaging array and a scintillator attached thereto.

In FIG. 1, an imaging array 170 can include an array of pixels 100. As shown, pixels 100 can include known photosensing elements 140 (e.g., photosensors, n-i-p photodiodes, p-n junction photodiodes, MIS photosensors, phototransistors, etc.), known switching elements 150 (e.g., MOS thin-film-transistors, junction field-effect-transistors, fully-depleted SOI transistors, partially-depleted SOI transistors, Silicon-on-glass transistors, bulk MOS transistors, bi-polar transistors, etc.), or read-out circuits (not shown), etc. The photosensing elements 140 and the switching elements 150 can be substantially co-planar. The imaging array 170 can optionally include a passivation layer 132 (e.g., thin encapsulation layer) for protection and/or isolation of the imaging array 170. In the related art, a silicon nitride layer or a silicon dioxide layer, which have a high dielectric constant, can be used as the passivation layer 132, however, such passivation layers are thin, typically less than 500 nm, and difficult to make thicker. An active surface of imaging array 170 can include, for example, topography between the highest and lowest point of about 1 µm to about 3 µm.

Also shown in FIG. 1 is low dielectric constant insulating layer 160 that can be formed over (e.g., encapsulate) the active surface of the imaging array 170 to provide a selected separation or fixed separation of the imaging array 170 from the scintillator 180. For example, the height of a low dielectric constant insulating layer 160 can be higher than the active surface of imaging array 170. Imaging array 170 can be formed on an insulating substrate such as a glass substrate 130. Also shown in FIG. 1 is scintillating screen 182 that can include a substrate 184 (referred to herein as scintillator 180). Scintillator 180 can be placed over the low dielectric constant insulating layer 160 and the imaging array 170 to form an integrated digital radiography detector 190. As used herein, the active surface of imaging array 170 is intended to include the surface of the imaging array 170 that faces the scintillator 180 and comprises pixels 100.

Active areas of the active surface of the imaging array 170 can include areas used for photosensing and remaining portions of the active surface can preferably provide potential locations for low dielectric constant second insulating layers. In exemplary embodiments, one or more low-dielectric constant insulator(s) can be coated on a radiographic array and patterned such that the thickness of the low-dielectric constant insulator over the photosensor (e.g., photodiode) is less than the thickness of the low-dielectric constant insulator over the non-photo-sensitive portions of a radiographic imaging array. However, as shown in FIG. 1, in one embodiment, the low dielectric constant insulating layer 160 can be a single insulating layer that can encapsulate the imaging array 170.

A scintillator 180 can be applied in close proximity of the imaging array 170 in order to convert X-rays into visible light. The distance between scintillator and imaging array is generally made as small as possible to improve detector array characteristics (e.g., reduce optical crosstalk between adjacent pixels). In some portable radiographic detectors, the scintillator may be deposited directly on the imaging array. Inventors of this application determined an interaction between a scintillator and data lines on a radiographic detector when the scintillator (e.g., deposited CsI scintillator) was in close proximity to the data lines. The CsI scintillator has high dielectric constant (e.g., 6.5) and can have ionic charge and finite resistivity.

Data lines 174 can be the largest source of noise in a DR detector, for example, where noise in electrons proportional to the data line capacitance times the square root of the data line resistance. One component of data line capacitance is an overlap capacitance between data lines 174 and gate lines 172. Two contributors to data line capacitance can be the overlap area between data lines 174 and gate lines 172 and the drain 151-to-gate 172 and source 152-to-lightshield 153 capacitance. In addition to these two components, a third contributor, which can be smaller, to the data line capacitance can be capacitance between bias lines 176 and data lines 174. Since the bias line 176 can be coupled to an anode 162 of photosensors or pin photodiode 161, an entire area of the anodes of all photosensors or photodiodes in a given column and adjacent columns can contribute to the capacitance between bias lines 176 and data lines 174.

Most scintillating materials have high dielectric constant. CsI, for example, can have a dielectric constant of 6.5. $Gd_2O_2S$ (GOS) particles coated with a binder can have a dielectric constant of about 4.8 The inventors of the application determined that the presence of the scintillator can significantly increase the capacitive coupling between bias line 176 and data line 174.

To reduce such capacitive coupling, a separation between scintillator and at least portions of an imaging array can be increased using an insulator. The lower the dielectric constant of the insulator, the greater the reduction in capacitance can be for a given thickness insulator. In contrast, since the optical crosstalk between pixels in the imaging array depends only on the insulator thickness, the capacitive coupling can be reduced or minimized for a given optical crosstalk by selecting a low dielectric constant insulator.

Conventional dielectrics used in flat panel processing, such as silicon nitride, have high dielectric constants. For example, silicon nitride has a dielectric constant of 7.5 and silicon dioxide can have a dielectric constant of 3.9.

According to embodiments of the application, embodiments of an insulating layer 160 with a dielectric constant less than 3.0, can include selective organic dielectrics. Exemplary embodiments of low dielectric constant insulating layer 160 can include high transparency to light emitted by the scintillator and an index of refraction corresponding to the imaging array/scintillator. For example, B-staged bisbenzocyclobutene-based (BCB) monomers can have a dielectric constant of 2.5-2.65, high transparency in the visible range and/or an index of refraction of 1.6, or acrylic can have a dielectric constant of 3.3, high transparency in the visible range, and/or an index of refraction of 1.49. Alternatively, porous inorganic dielectrics with low dielectric constants can be used. Another material with a low dielectric constant that can be used is SUB. In one embodiment, dielectric constants of a first dielectric layer or a second dielectric layer can be less than 2.8, less than 2.6, less than 2.4, or less than 2.0.

Figure 2:
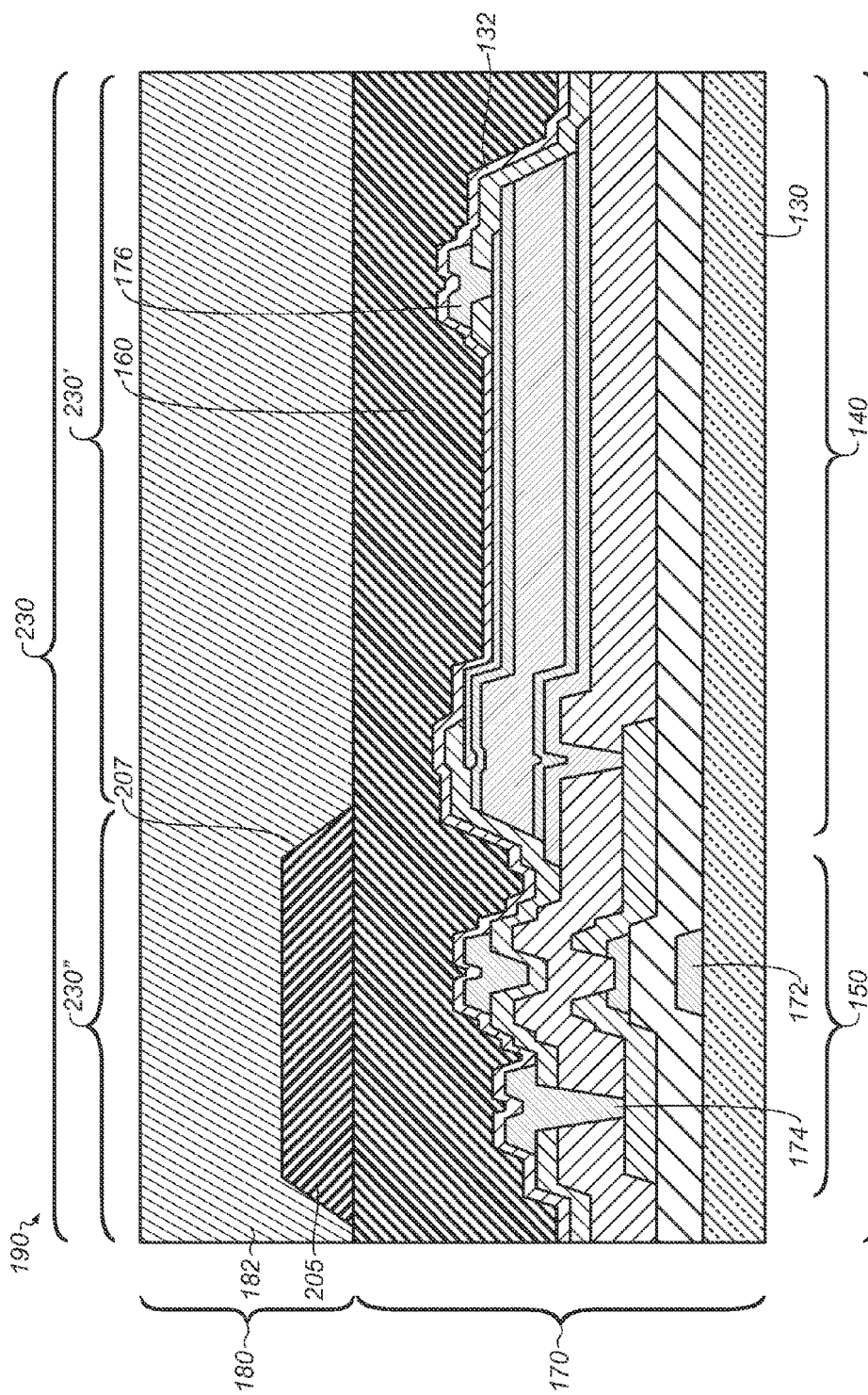
FIG. 2 is a diagram that shows a cross-section of another embodiment of a combined radiographic scintillator and imaging array according to the application.

FIG. 2 is a diagram that shows another embodiment of a DR imaging array according to the application. As shown in FIG. 2, a dual-layer dielectric (e.g., first and second low dielectric constant insulating layers) or a selectively thinned single-layer dielectric can be used. As shown in FIG. 2, a first dielectric or first low dielectric constant insulating layer 160 can be over the photo-sensor to achieve high optical coupling and low cross-talk and both the first dielectric and the second dielectric 205 can over the non-photo-sensitive portion of the array to reduce capacitive coupling. Alternatively, a single dielectric 230 (not shown) can be made thinner 230' over the photo-sensor to achieve high optical coupling and low cross-talk and the single dielectric 230 can be thicker 230" over a non-photo-sensitive portion of the imaging array 170 to reduce capacitive coupling. Alternatively, the first dielectric 160 can be thin and over the photo-sensor and the second dielectric 205 can be thicker and over the non-photo-sensitive portions of the imaging array 175. In one embodiment, the scintillator 180 preferably can be directly deposited on the first and second low dielectric constant insulating layers (e.g., 160 and 205 or 230, such as by evaporation for CsI or by coating for GOS).

In one embodiment, second low dielectric constant insulating layers 205 can be wider/larger at a lower surface (horizontal cross-section) or bottom surface than at an upper surface or top surface. The second dielectric 205 can have a sloped transition 207 from a top surface to lower surface, which can improve attachment of the scintillator to the imaging array. The transition 207 can be linear or non-linear. For example, second dielectric 205 having tapered sides can improve performance characteristics and/or simplify manufacturing processes.

In one model used to analyze an exemplary imaging array for a radiographic detector, a low dielectric constant layer reduced a capacitive interaction for a scintillator and an imaging array. Exemplary interactions are shown below. Table 1 shows the dielectric constant for four different encapsulation materials; the dataline capacitance per pixel for an array with no encapsulant material and a CsI scintillator; the dataline capacitance per pixel for an array with 2 µm of the encapsulant material and the CsI scintillator; the dataline capacitance per pixel for the same array with an additional 20 µm of BCB patterned over the 2 µm encapsulant material. Table 1 shows that as dielectric constant of material drops the data line capacitance per pixel can be reduced.

TABLE 1

| | Encapsulant | | | |
| --- | --- | --- | --- | --- |
| | SiN | PolyCarbonate | Acrylic | BCB |
| Dielectric Constant | 7 | 4 | 3.3 | 2.6 |
| No Encapsulant | 31.5 | 31.5 | 31.5 | 31.5 |

TABLE 1-continued

| | Encapsulant | | | |
| --- | --- | --- | --- | --- |
| | SiN | PolyCarbonate | Acrylic | BCB |
| 2 um Encapsulant | 32.8 | 29.6 | 28.7 | 27.8 |
| Plus 20 um Patterned BCB | 30.5 | 27.7 | 27.1 | 26.3 |

Table 2 shows the dataline capacitance per pixel for three configurations, (a) no encapsulation between a CsI scintillator and an array, (b) a 20 μm acrylic encapsulation between the CsI scintillator and the array, and (c) a 2 μm acrylic encapsulation with an additional 20 μm of BCB patterned to cover the data line between the CsI scintillator and the array. Table 2 shows that by adding low dielectric constant material over the data line, the capacitance can be further reduced without significant impact to QE.

TABLE 2

| | Data Line Capacitance Per Pixel (fF/pix) | Pixel QE (CsI Scinitllator) |
| --- | --- | --- |
| (a) No Encapsulation | 31.5 | 51.3 |
| (b) 20 um Acyrlic | 27.3 | 50.2 |
| (c) 2 um Acrylic + 20 um BCB | 27.1 | 50.2 |

Figure 3:
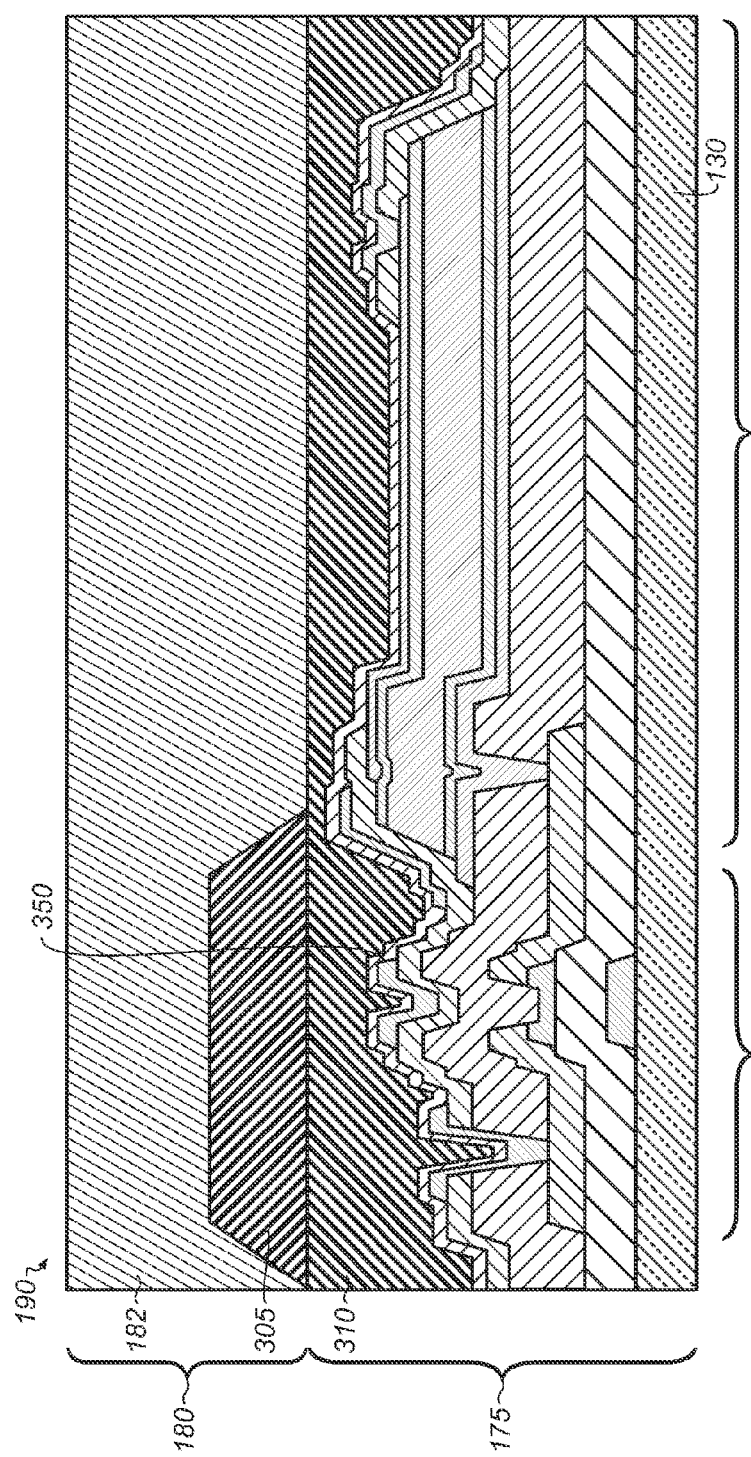
FIG. 3 is a diagram that shows a cross-section of another embodiment of a combined scintillator and imaging array according to the application.

FIG. 3 is a diagram that shows another embodiment of a DR imaging array according to the application. As shown in FIG. 3, second low dielectric constant insulating layer 305 can be opaque to visible light. For example, the second dielectric layer 305 can be an opaque organic dielectric layer. As shown in FIG. 3, first low dielectric constant insulating layer 310 can be over the photo-sensor to achieve high optical coupling and low cross-talk and both the first dielectric 310 and the second dielectric 305 can be over the non-photosensitive portion of the array to block impinging light and/or reduce capacitive coupling.

Opacity or a light-blocking condition for the second low dielectric constant insulating layers 305 can be achieved in a number of exemplary ways, including but not limited to: incorporation of pigment in the second low dielectric constant insulating layers 305 prior to coating and patterning, incorporation of dye in the second low dielectric constant insulating layers 305 prior to coating and patterning, use of photoactive or thermally-active materials in the second low dielectric constant insulating layers 305 that become opaque upon exposure to light or heat, and/or dye diffusion into the second low dielectric constant insulating layers 305 following coating and patterning (e.g., similar to color filters on image sensors). Alternatively, the second low dielectric constant insulating layers 305 can contain mordants that bind a dye and the first low dielectric constant insulating layers 310 can contain a dye-blocking layer.

Opaque as used herein can include materials that absorb light or reflect light. Absorbing opaque materials can have an exemplary absorption of equal to or greater than about 60%, 80%, or 90% in an exemplary 1-10 micron thickness of the second dielectric layer 305. Colorants, as used herein can include, dyes, pigments, etc., that can be incorporated into exemplary embodiments of low dielectric constant insulating layers (e.g., the second dielectric layer 305) not over the photosensor areas of imaging array 175 to increase opacity or reduce an amount of scintillator light there through. For example, the second dielectric layer 305 can include opaque materials or at least one surface of thereof can include opaque materials. For example, dye or pigment may be diffused into or transferred onto the surfaces (e.g., side surfaces or a top surface) of the second dielectric layer 305, such as by techniques used to form color filter arrays for displays. Absorbing materials (e.g., colorants, etc.) for the second dielectric layer 305 can be used to reduce optical crosstalk caused by light piping between the imaging array 175 and the scintillator 180.

Figure 4:
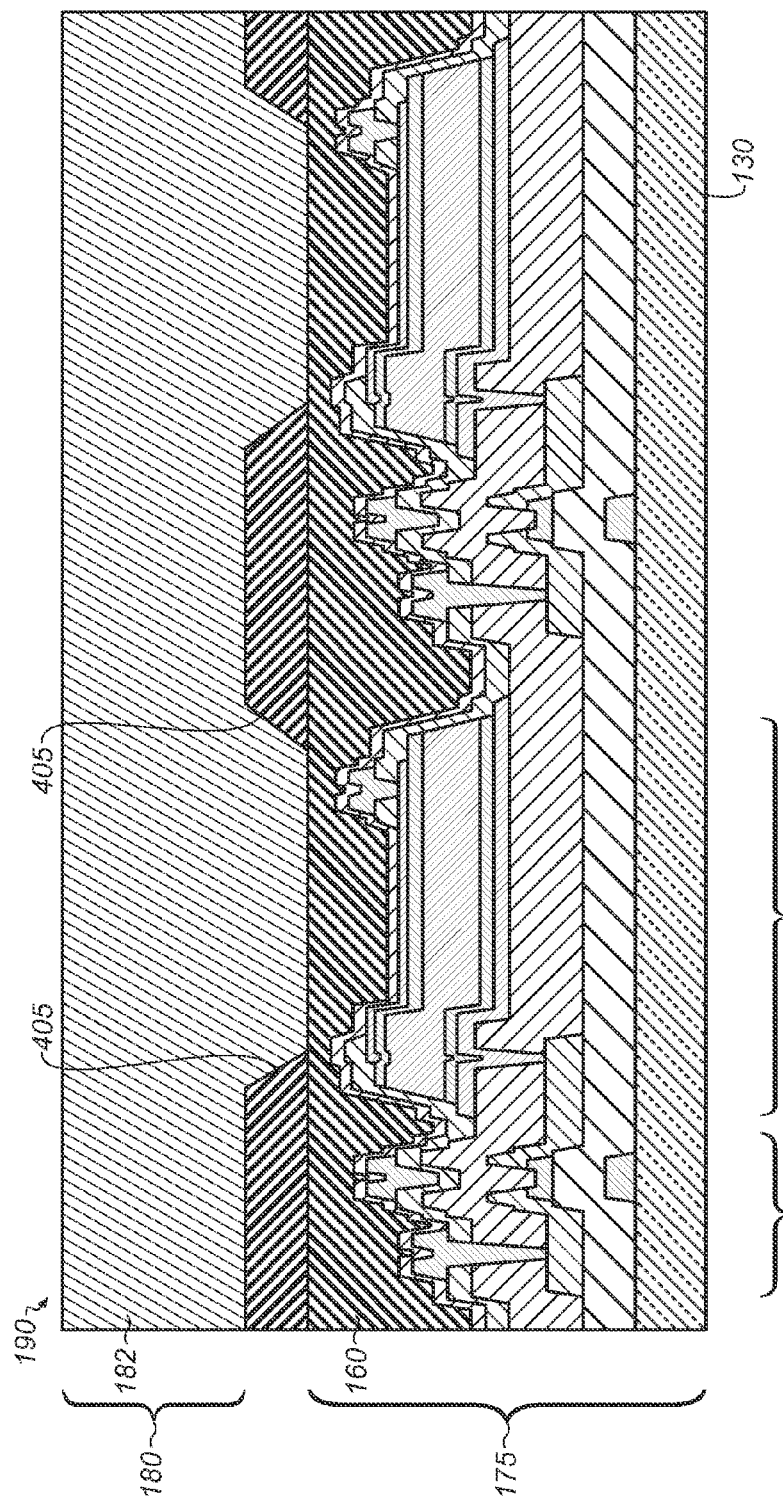
FIG. 4 is a diagram that shows a cross-section of another embodiment of a combined scintillator and imaging array according to the application.

FIG. 4 is a diagram that shows another embodiment of a DR imaging array according to the application. As shown in FIG. 4, light-blocking dielectric layer can be patterned to block the scintillator 182 light from impinging the TFT 150. Various related art TFTs 150 can be light-sensitive and/or can suffer long-term degradation of performance characteristics under prolonged exposure to light. To reduce or prevent such deleterious effects form light, a light shield 350 (FIG. 3) can be arranged between the TFT 140 and the scintillator 182. Exemplary light shields can be implemented in related art DR imaging array metal layers. A metallic light shield, however, can increase the data line capacitance, and can thereby increase sensor noise. A substantially opaque low dielectric constant insulating layer can be added to or replace the lightshield, which can thereby reduce data line capacitance, and/or reduce imaging array 175 noise.

An embodiment of a combined scintillator and imaging array can use an opaque low dielectric constant layer 405 and can include a pixel configuration that does not include a metallic light shield. As shown in FIG. 4, the second light-blocking dielectric 405 can optionally extend over an edge of a PIN photodiode to reduce image lag that can be caused by interface states at the PIN photodiode edge. The second light-blocking dielectric 405 can also extend over areas where illumination (e.g., light) from the scintillator 182 is not absorbed or reflected by the imaging array 175. Exemplary embodiments of a second light-blocking dielectric 405 can use colorant therein to reduce light transmission into imaging array 175 or the substrate 130, with consequent light scattering to adjacent photosites and/or loss of resolution.

Figure 5:
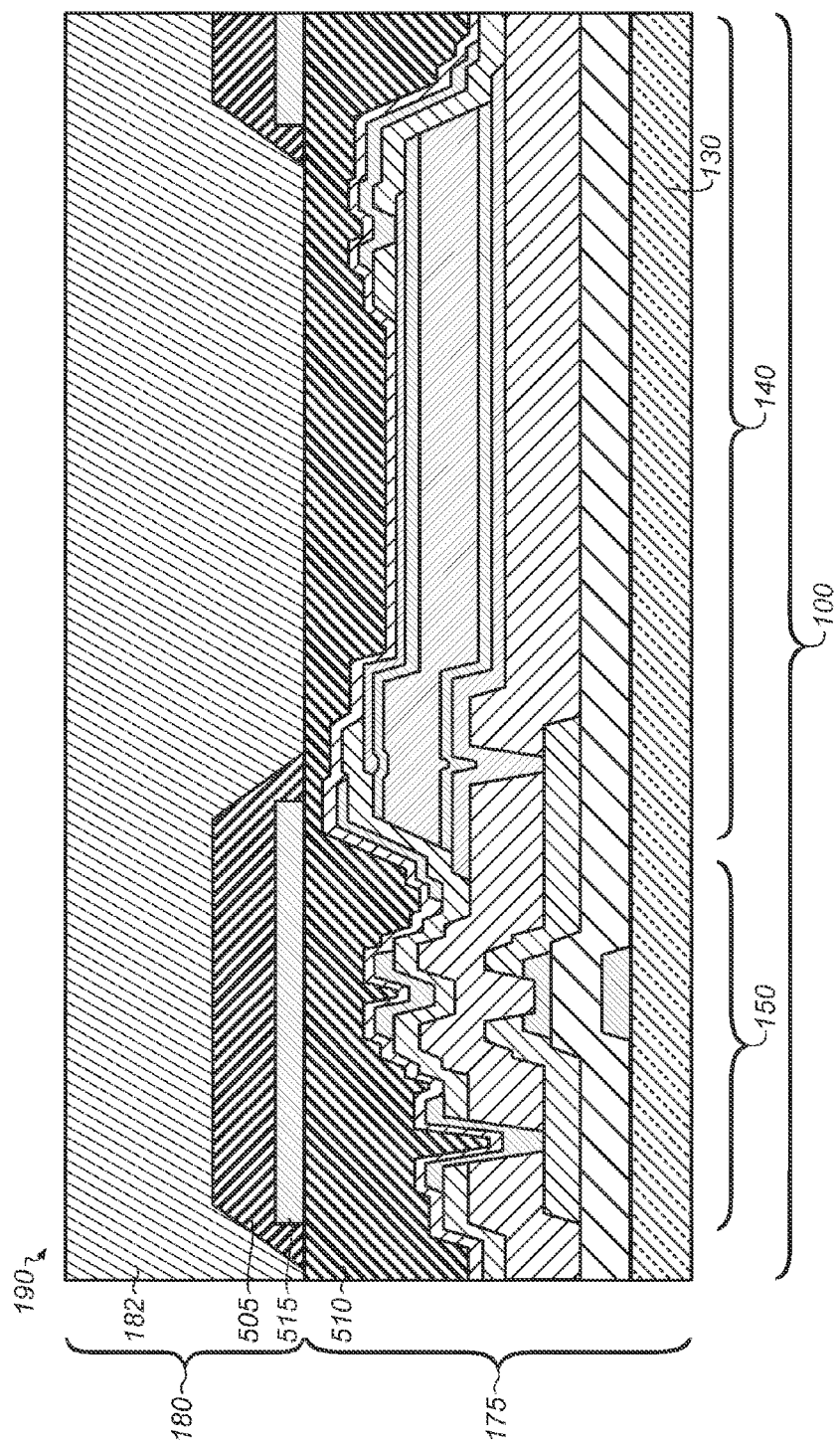
FIG. 5 is a diagram that shows a cross-section of an embodiment of a radiographic detector configured to include a combined scintillator and imaging array according to the application.

FIG. 5 is a diagram that shows a cross-section of an embodiment of a radiographic detector configured to include a combined scintillator and imaging array using a low dielectric constant material in between. As shown in FIG. 5, a third layer 515 can be formed or placed above/between as first low dielectric constant insulating layer 510 and a second low dielectric constant insulating layer 505. The low dielectric constant insulating layers 510 and 505 can be the same or different material. The third layer 515 can be conductive (e.g., an electrostatic shield), partially conductive, and/or insulating but opaque. An opaque layer for the third layer 515 can provide light shielding of the pixel readout circuitry. A conducting layer for the third layer 515 can provide electrostatic shielding of the pixel readout circuitry. In one embodiment, the third layer 515 (e.g., conductive) can be on top of or over the second low dielectric constant insulating layer 505.

Figure 6:
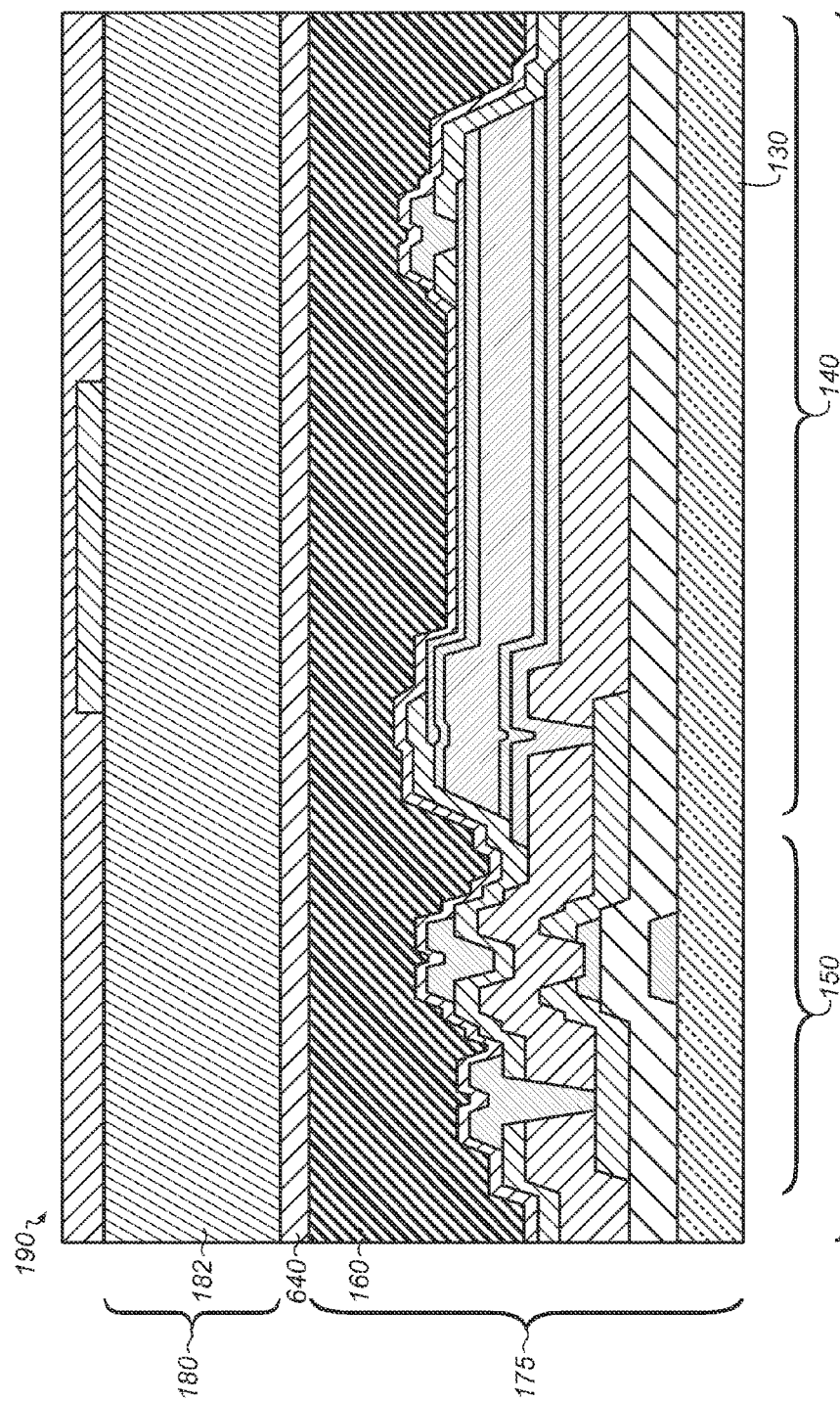
FIG. 6 is a diagram that shows a cross-section of an embodiment of a radiographic detector configured to include a combined scintillator and imaging array according to the application.

FIG. 6 is a diagram that shows a cross-section of an embodiment of a radiographic detector configured to include a scintillator and imaging array using a low dielectric constant material in between. In one, some, or all exemplary embodiments, an anti-static layer can be included between the scintillator and the imaging array. For example, an anti-static layer can be positioned between the array layers and the scintillator (e.g., coated on the array after fabrication and patterned). As shown in FIG. 6, an anti-static layer 640 can reduce or prevent ESD damage to the imaging array 175 from static generated during attachment of the scintillator 180, coating of the scintillator 180, or during use caused by, for example, tribo-electric charging between scintillator and an insulator. Since the anti-static layer 640 can also increase capacitance between dataline and bias line, embodiments of a low dielectric constant insulators can help to reduce or minimize the capacitance for a given thickness insulator.

In one embodiment, GOS scintillator sheets can be attached to the imaging array using an adhesive. For example, an adhesive thickness can be 5 to 10 microns. Alternatively, the adhesive can be roughly equivalent in thickness to the low dielectric constant encapsulation or thicker than the low dielectric constant encapsulation. Further, the adhesive can be coated on the scintillator. In one embodiment, an antistat can be coated on the scintillator before the adhesive is coated on the scintillator. In some embodiments, a surface of the low dielectric encapsulation can be coated with an anti-stat and/or include anti-stat material in the formulation of the adhesive. In another embodiment, the GOS scintillator can be coated directly on the imaging array, which can be preferable to address large height differences in the low dielectric encapsulation (e.g., first dielectric and second dielectric).

In certain exemplary embodiments, the dielectric properties of the adhesive can also be considered (e.g., alone or in combination with other layers used to attach the scintillator to the imaging array). In one embodiment, the dielectric properties of the adhesive layer and in combination with dielectric properties of the low dielectric constant encapsulation can be used to achieve a selected property or prescribed dielectric requirement of the encapsulation of the imaging array 170. For example, a dielectric property of the low dielectric encapsulation or a combined dielectric property of the adhesive and the low dielectric encapsulation can be to limit an increase in capacitance or in data line capacitance caused by the scintillator to be no more than a 5%, 10%, or 20% increase in capacitance caused by the data line and the scintillator.

In exemplary embodiments, additional features of couplings between scintillator/imaging array of a detector can be used. For example, Table 3 provides exemplary combinations for features used with/for insulating layers of exemplary embodiments of methods and/or apparatus herein.

TABLE 3

|  | Data line | Photosensor or photodiode |
| --- | --- | --- |
| Dielectric constant | Low | Not Applicable (N/A) |
| Refractive index | N/A | High |
| Thickness | Thick | Thin |
| Transparency | NA or opaque | High |
| Antistat layer | No | Yes |

In some embodiments, length and width (or height) of low dielectric constant insulators or insulating layers can be limited by processes (e.g., minimum feature size, critical dimensions) used to define the insulators. For photo-lithographical manufactuiring, typical flat-panel process capability would require a minimum length and width of approximately 3 microns.

Selected thickness or maximum thickness of exemplary low dielectric constant layers can be determined by the loss in resolution caused by lateral scattering of light (e.g., light-piping) between the active surface of the imaging array and the opposing surface of the scintillator. Thicknesses for exemplary embodiments of low dielectric constant layers can be 10 microns or less for 150 micron pixel dimension. In exemplary embodiments of low dielectric constant layers, thickness can be 15 microns or less, 5 microns or less, 3 microns or less, or 1 micron or less.

According to exemplary embodiments, an adhesive layer (not shown) can be added to a surface of embodiments of low dielectric constant insulating layers to form a bond to the surface of the scintillator layer 180 facing the imaging array 170, 175. Alternatively or in addition, a passivation layer (not shown) can be included on the active surface of the imaging array 170, 175, and embodiments of low dielectric constant insulating layers can be formed (e.g., over) the passivation layer (not shown).

Embodiments of radiographic detector arrays 190 can reduce problems caused by noise generated by interactions between the scintillator 180 and/or elements in the imaging array 170, 175. By reducing noise caused by the scintillator 180 in relation to the imaging array 170, 175, embodiments of radiographic digital detector arrays 190 can include improved imaging characteristics.

Lateral scattering of light caused by reflections off the active surface of the imaging array and the scintillator can result in loss of resolution can be improved by using the opaque second low dielectric imaging layers. While reducing or preventing crosstalk, the opaque second low dielectric imaging layers also can reduce the signal level because of the optical absorption of the light emitted from the scintillator 180. It will be appreciated that incorporation of colorants in photo-patternable materials can block the UV wavelengths used for photolithography and therefore the colorants that are substantially transparent to UV but opaque in the visible spectrum can be used. Alternatively, an opaque material may be patterned using photoresist and the pattern in the photoresist transferred to the spacer material by subsequent wet etching or dry etching of the underlying spacer material.

Embodiments of detector arrays 190 including first and/or second low dielectric imaging layers can be manufactured in many ways, the embodiments discussed herein are various example methods (e.g., photo-patternable or etching, for example, ion beam milling, reactive ion etching), but are not intended to be limiting. It will be appreciated that photolithography techniques, anisotropic etching techniques, isotropic etching techniques, various deposition techniques, etc. are well known in the art and the techniques can be adjusted as required to obtain desired results herein. Further, detector arrays and the methods of manufacturing detector arrays are generally known.

As will be obvious to one of ordinary skill in the art, the various embodiments can be combined to form many different combinations, all of which are intended to be incorporated by this disclosure. In one embodiment, exemplary scintillator 180 and/or imaging array 170, 175 can be coated with additional optional layers (e.g., a protective layer). As will be obvious to one of ordinary skill in the art, the various embodiments can be combined to form many different combinations, all of which are intended to be incorporated by this disclosure.

Figure 7:
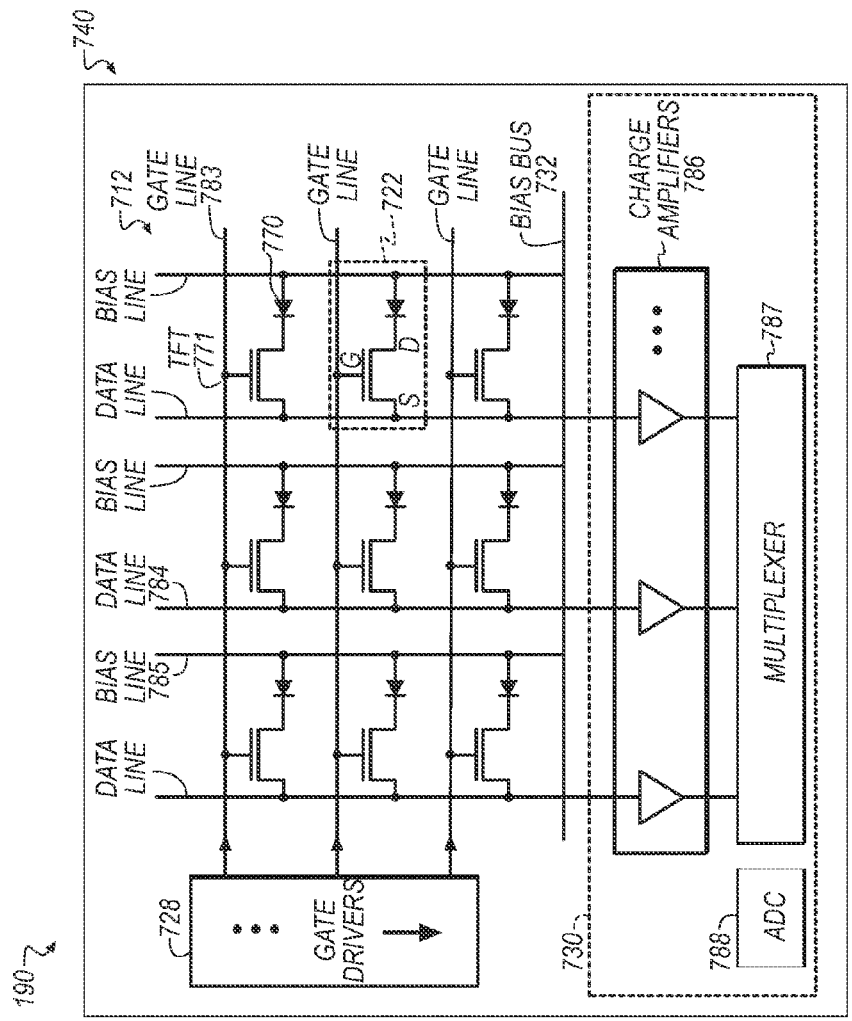
FIG. 7 is a diagram that shows a schematic of a portion of an imaging array for a radiographic detector capable of using embodiments of low dielectric constant insulating layer between a scintillator and imaging array according to the application.

FIG. 7 is a diagram that shows a schematic of a portion of an imaging array for a radiographic detector capable of including embodiments of a low dielectric insulating layer described herein. FIG. 7 is also a diagram that shows a schematic of a portion of an imaging array for a radiographic detector capable of including embodiments of an anti-static layer according to embodiments herein. In certain exemplary embodiments, an imaging array for a radiographic detector can include combinations of embodiments of anti-static layers (e.g., patterned) and/or embodiments of low dielectric insulating layers. As shown in FIG. 7, a schematic of a portion of an exemplary flat panel imager 740 can include an array 712 with a number of pixels such as pixels 722 including a-Si:H n-i-p photodiodes 770 and TFTs 771. Gate driver chips 728 can connect to the blocks of gate lines 783, readout chips 730 can connect to blocks of data lines 784, and bias lines 785 can connect to a bias bus 732 or variable bias reference voltage. Charge amplifiers 786 can be provided that receive signals from the data lines 784. An output from the charge amplifiers 786 can go to an analog multiplexer 787 or directly to an analog-to-digital converter (ADC) 788 to stream out the digital image data at desired rates.

Figure 8:
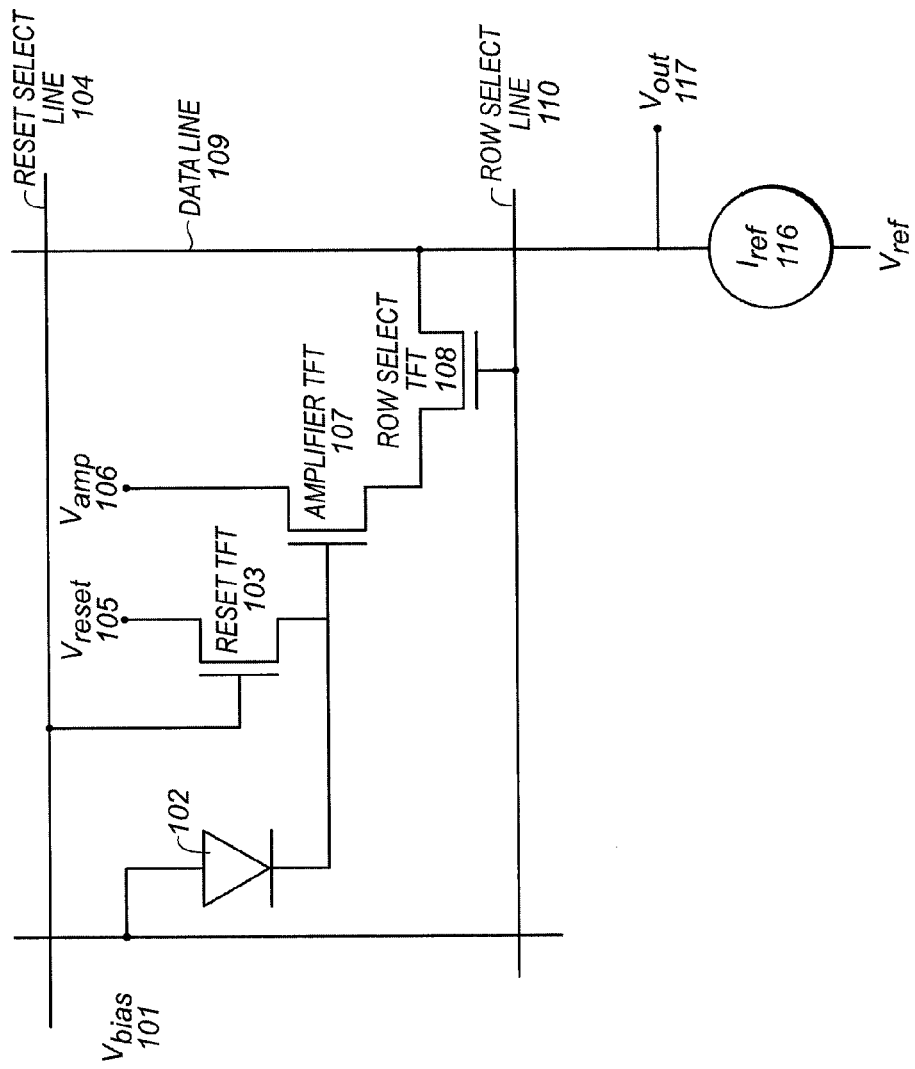
FIG. 8 is a diagram that shows a schematic of a portion of an imaging array for a radiographic detector capable of using embodiments of low dielectric constant insulating layer between a scintillator and an imaging array including active pixels according to the application.

In another embodiment, the imaging array can comprise active pixels, in which an amplifier is provided for converting the voltage on the photosensor to a current. Several designs for active pixel are well known to those skilled in the art, including 3-transistor, 4-transistor and shared-transistor designs. An exemplary 3-transistor design is illustrated in FIG. 8. A pixel can include a photodiode 102, a bias supply line 101, an amplifier TFT 107, and a row select TFT 108 addressed by the row select line 110, a reset TFT 103 addressed by the reset select line 104 as shown in FIG. 8. Biases Vamp 106 and Vreset 105 can be supplied external to the pixel. In operation, the cathode of the photodiode 102 can be reset to a voltage Vreset by enabling the reset select line 104, thereby turning the reset TFT 103 into a conducting state. Following reset, the imaging array is exposed to light. The exposure causes the potential between the anode and the cathode of the photodiode to decrease, thereby causing the voltage on the gate of the amplifier TFT 107 to change. Following exposure, the signal can be read out by enabling the row select line 110, connecting the amplifier TFT 107 to the data line 109 and causing a current to flow from the amplifier bias Vamp 106 to the dataline 109. This current may be sensed in a number of ways. In one exemplary method, a reference current can be supplied to the dataline 109 by a reference current generator 116. A current minor circuit is commonly used for the current generation. The voltage Vout 117 on the dataline is sensed, often with a voltage sampling circuit internal or external to the array. Following signal sensing, the photodiode can be reset by enabling the reset TFT. The signal on the dataline can be sensed a second time, with the exposure of the photodiode determined by the difference between the signal on the dataline 109 before and after reset. In a second exemplary method, the current is integrated by a charge amplifier external or internal to the imaging array.

One limitation to readout speed in active pixel imaging arrays realized in radiographic detectors or flat-panel TFT technology is the rise time of the signal on the dataline 109. Referring to the readout method of FIG. 8, the rise time of the signal on the dataline increases in proportion to the dataline capacitance. Using a low dielectric constant organic material, such as BCB, between the array and the scintillator can enable increased readout speed active pixel radiographic detectors.

One limitation to readout speed in active pixel imaging arrays realized in flat-panel TFT technology is the rise time of the signal on the dataline 109. Referring to readout of imaging array of FIG. 8, the rise time of the signal on the dataline increases in proportion to the dataline capacitance. Using a patterned anti-static material over the imaging array or between the imaging array and the scintillator can allow readout speeds to be comparable to active pixel radiographic detectors lacking the patterned anti-static material.

Figure 9:
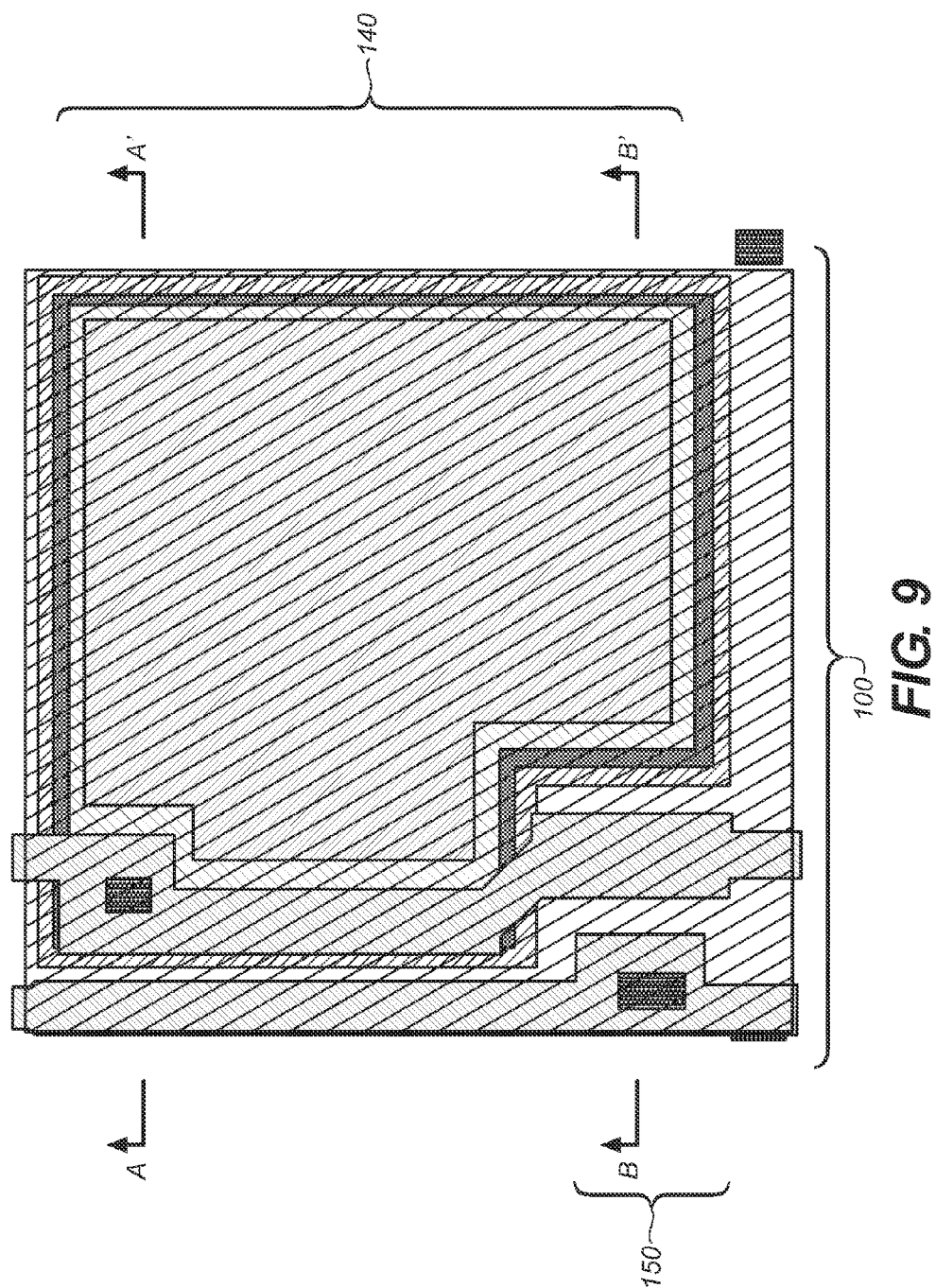
FIG. 9 is a diagram that shows a top view of an embodiment of a radiographic detector imaging array that is configured to include a scintillator and is capable of using embodiments of low dielectric constant material therebetween as described herein.
Figure 10:
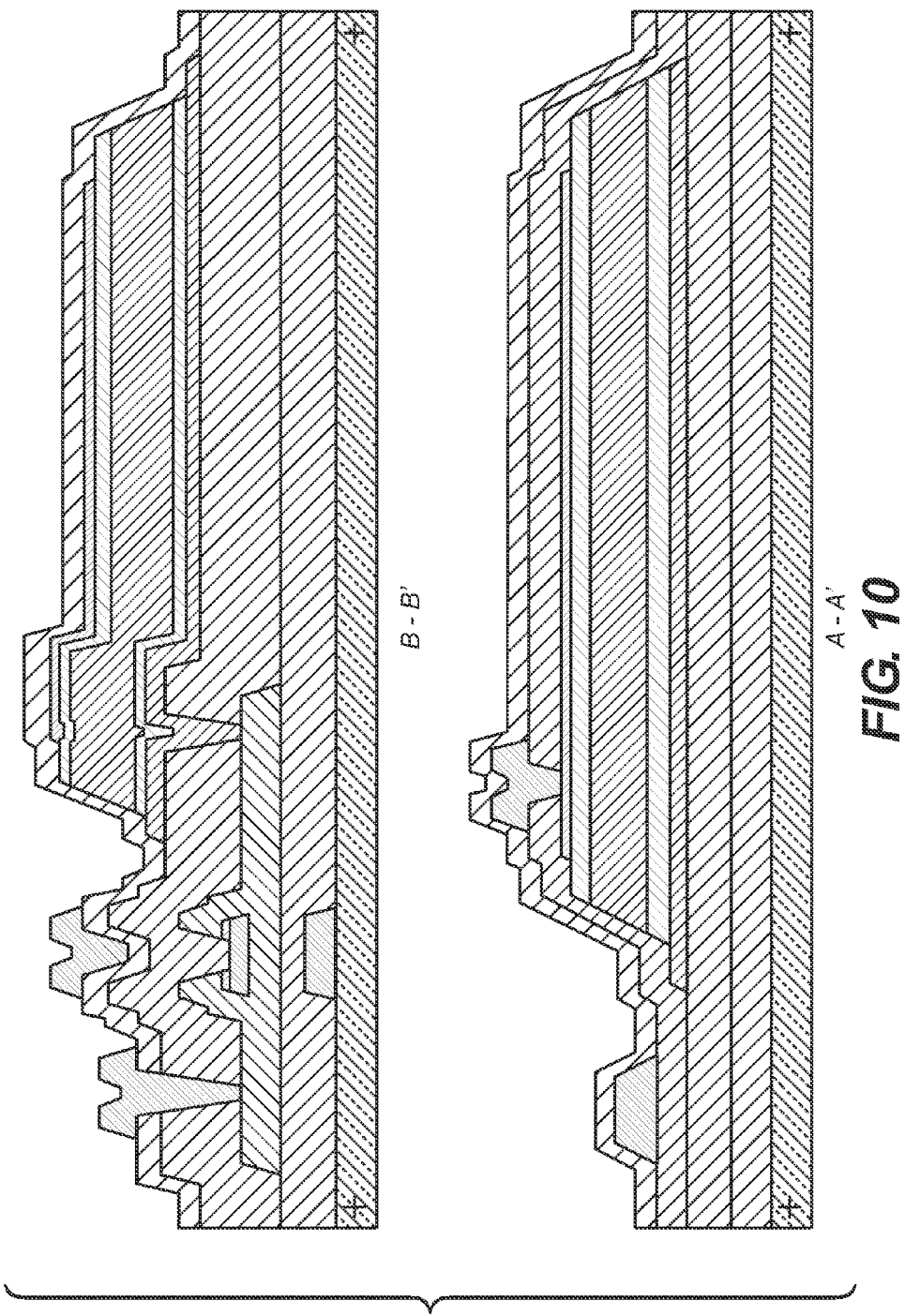
FIG. 10 is a diagram that shows cross-sections of the imaging array as shown in FIG. 9 along lines A-A' and B-B'.

FIG. 9 is a diagram that shows a top view of an embodiment of a radiographic detector imaging array that is configured to include a scintillator (not shown) and is capable of using embodiments of an intermediate layer such as low dielectric constant material therebetween as described herein. FIG. 10 is a diagram that shows cross-sections of the imaging array as shown in FIG. 9 along lines A-A' and B-B'.

Figure 11:
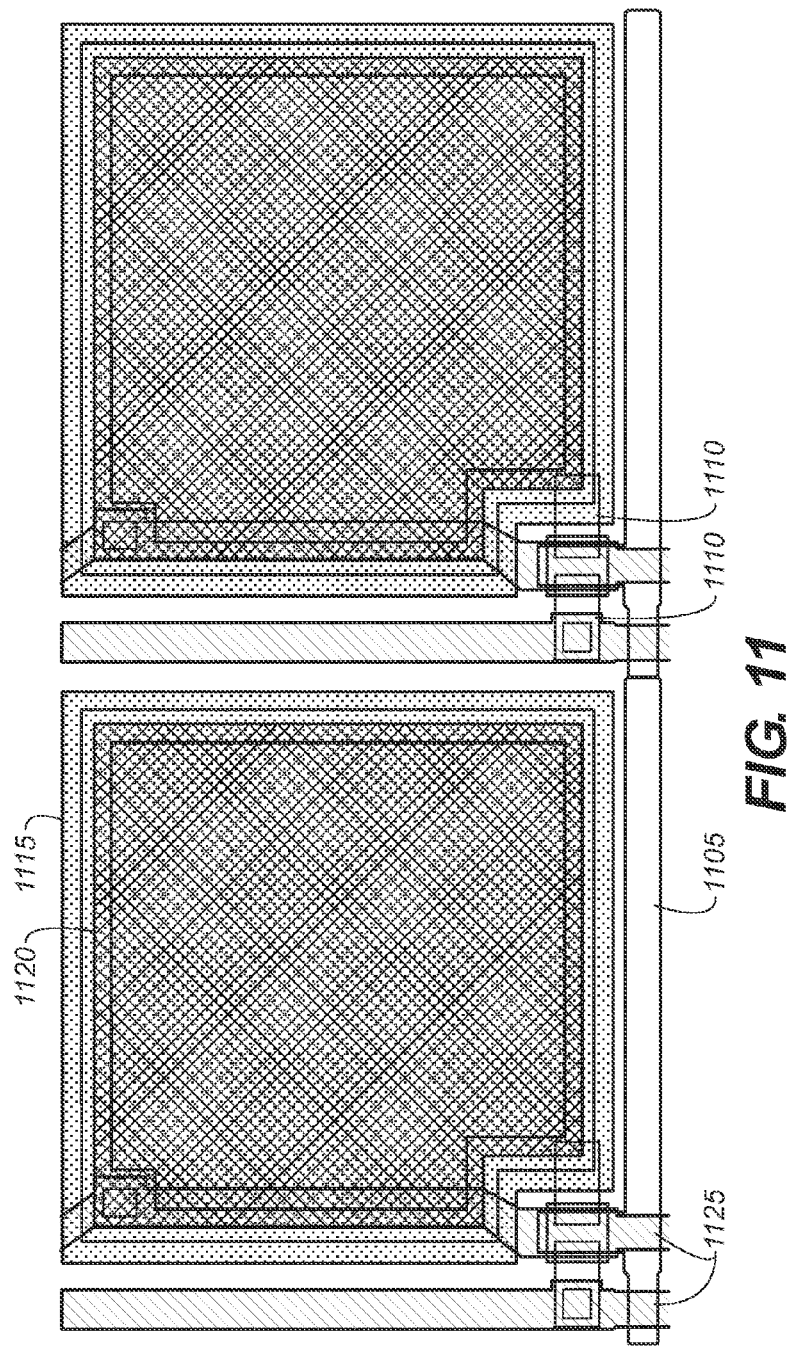
FIG. 11 is a diagram that shows a top view of conductive layers in an embodiment of a radiographic detector imaging array.

FIG. 11 is a diagram that shows a top view of conductive layers in an embodiment of a radiographic detector imaging array that can include a scintillator (not shown) and is capable of using embodiments of an intermediate layer such as low dielectric constant material therebetween as described herein. As shown in FIG. 11, a first conductive/metal layer 1105 can include a gate line, a second conductive/metal layer 1110 can include a source and drain for TFT transistor, a third conductive/metal layer 1115 can include a lower electrode for a photosensor, a fourth conductive/metal layer 1120 can include an upper electrode for a photosensor, and a fifth conductive/metal layer 1125 can include a bias line and data line. Pixel capacitance or imaging array capacitance can be affected by interactions between such exemplary conductive/metal layers or such exemplary conductive/metal layers and a scintillator.

Radiographic imaging arrays are known to be sensitive to electrostatic charge. Electrostatic charge can degrade the performance of radiographic arrays in a number of ways. First, for example, electrostatic charge resident at or in proximity of the imaging array can change the leakage characteristics of thin-film transistors used in pixel address circuitry. Second, electrostatic charge resident at or in proximity of the photosensor can cause changes in the surface potential of the photosensor sidewall, thereby increasing leakage current, increasing image lag, and/or leading to low-frequency noise. Third, in more severe cases, electrostatic charge can cause permanent damage to TFTs, thereby causing a short circuit or an open circuit between the photosensor and the data line. Fourth, in more severe cases, electrostatic charge can cause permanent damage to the photodiodes, thereby causing a short circuit or an open circuit in the photodiode.

Figure 12A:
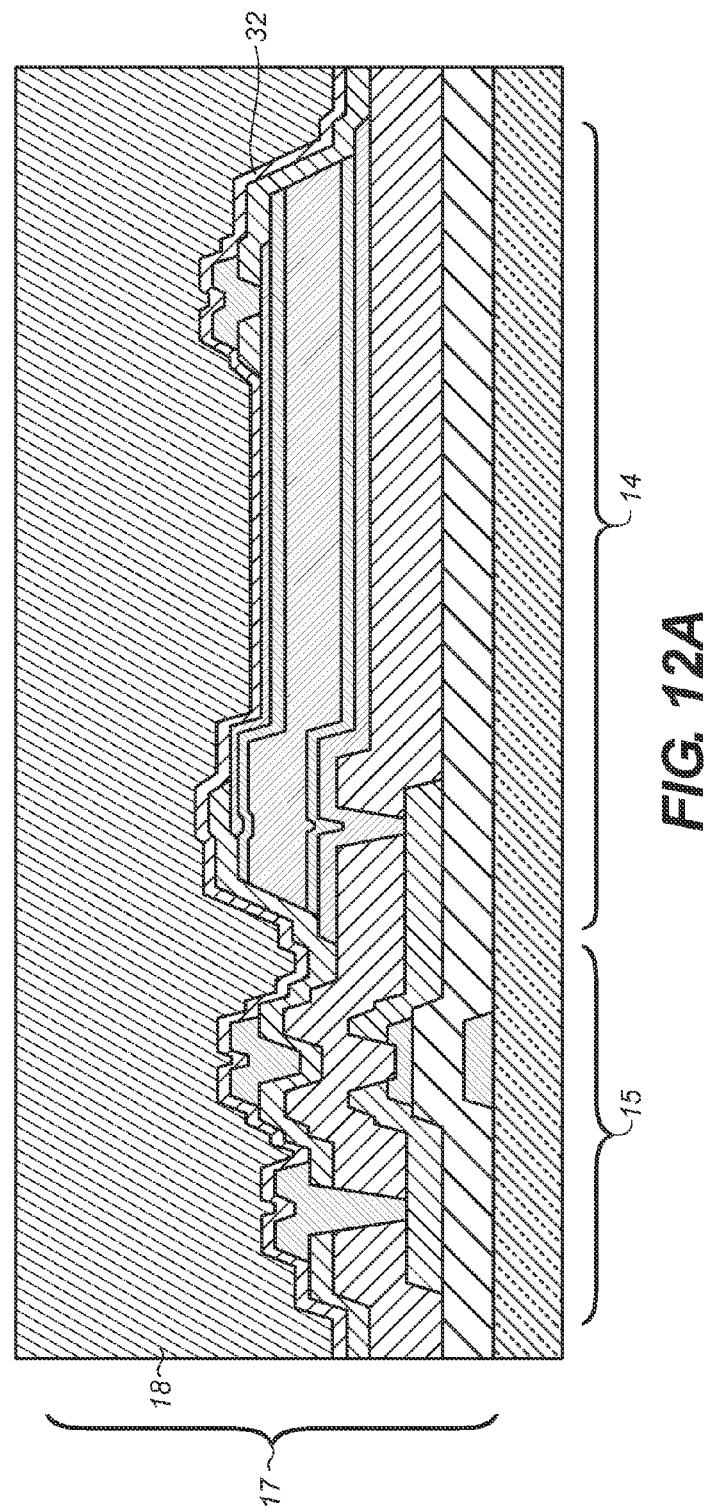
FIG. 12A is a diagram that shows a cross-section of a related art radiographic detector configured to include a combined scintillator and imaging array.

FIG. 12A is a diagram that shows a related-art pixel of an imaging array with mesa PIN photodiode 14 and TFT switch 15. As shown in FIG. 12A, a scintillator 18 is in direct contact with a top layer 32, typically a thin inorganic layer such as silicon nitride, of an imaging array 17. A scintillator 18 can be a scintillating sheet pressed against the imaging array 17, such as a sheet of Gd2O2S scintillating material, or deposited on the imaging array 17, such as evaporated CsI.

Figure 12B:
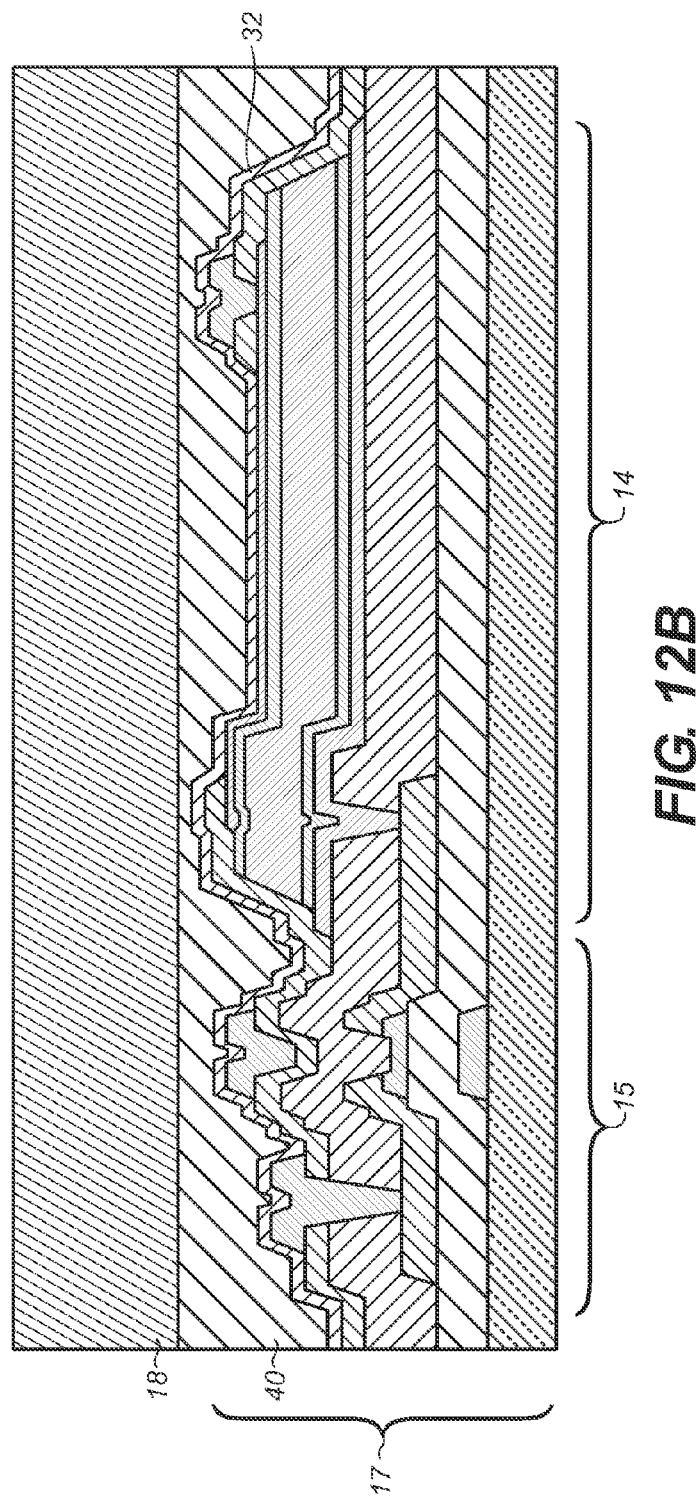
FIG. 12B is a diagram that shows a cross-section of another related art radiographic detector configured to include a combined scintillator and imaging array.

FIG. 12B is a diagram that shows another related-art pixel of an imaging array with mesa PIN photodiode 14 and TFT switch 15. As shown in FIG. 12B, an organic encapsulation layer 40 is coated over the imaging array 17 to provide physical and chemical protection of the imaging array 17 from damage from a scintillator 18.

Related-art radiographic imaging arrays employ electrostatic discharge (ESD) protection diodes on address lines (such as datalines and bias lines) and/or on readout lines to reduce voltage swing on these lines, thereby reducing ESD damage. However, related-art radiographic imaging arrays did not provide ESD protection internal to pixels in the imaging array.

The electrostatic charge can have a variety of sources, including but not limited to, first, tribo-electric charge generated by movement of the scintillator on the imaging array or movement of the scintillator on encapsulation over the imaging array. Second, charge can be generated during coating of the scintillator on the imaging array in arrays in which coated scintillators rather than attached scinitillators are employed. Third, charge can be generated during cleaning or handling imaging arrays, such as from water evaporation, water-spraying, air-spraying, or touching the imaging array with human or mechanical means. Fourth, charge on the surface of the scintillator material (e.g., scintillator sheets are insulating and can hold electrostatic charge for long periods of time). Scintillator materials (e.g., deposited) can contain fixed positive or negative charge.

There are a number of ways in which electrostatic charge can impact operations of photosensors including but not limited to, first, positive charge along the photodiode sidewall can cause an increase in electron flow along the sidewall, thereby increasing the leakage current. Second, positive charge can also increase the low-frequency (e.g., flicker) noise resulting from trapping and de-trapping of electrons at or near the sidewall.

Further, the charge level can be unstable, depending on exemplary environmental conditions such as humidity or temperature. Such unstable charge levels can result in instability in imaging array calibration or, in some cases, cause the imaging array to fail to meet performance specifications for radiographic imaging.

Exemplary embodiments according to the application are shown in FIG. 13 through 20.

Certain exemplary embodiments of systems and/or methods herein include radiographic detector arrays that can include a continuous anti-static material (e.g., a first anti-static layer) positioned over an imaging array or between at least a portion of an imaging array (e.g., photosensor) and a scintillating material. For example, embodiments of a continuous anti-static material can between at least a portion of the array and a scintillating material to reduce or prevent electrostatic charge. Embodiments of radiographic detector arrays and methods can further include providing electrical contact to the anti-static material. In one embodiment, the electrical contact can be made within pixels of the imaging array.

Anti-static materials can be defined as materials with resistivity between $1 \times 10^4$ Ω/square and $1 \times 10^{10}$ Ω/square. At resistivity $<1 \times 10^4$ Ω/square, the material can be considered a conductor and at resistivity $>1 \times 10^{10}$ Ω/square, the material can be considered an insulator.

Figure 13:
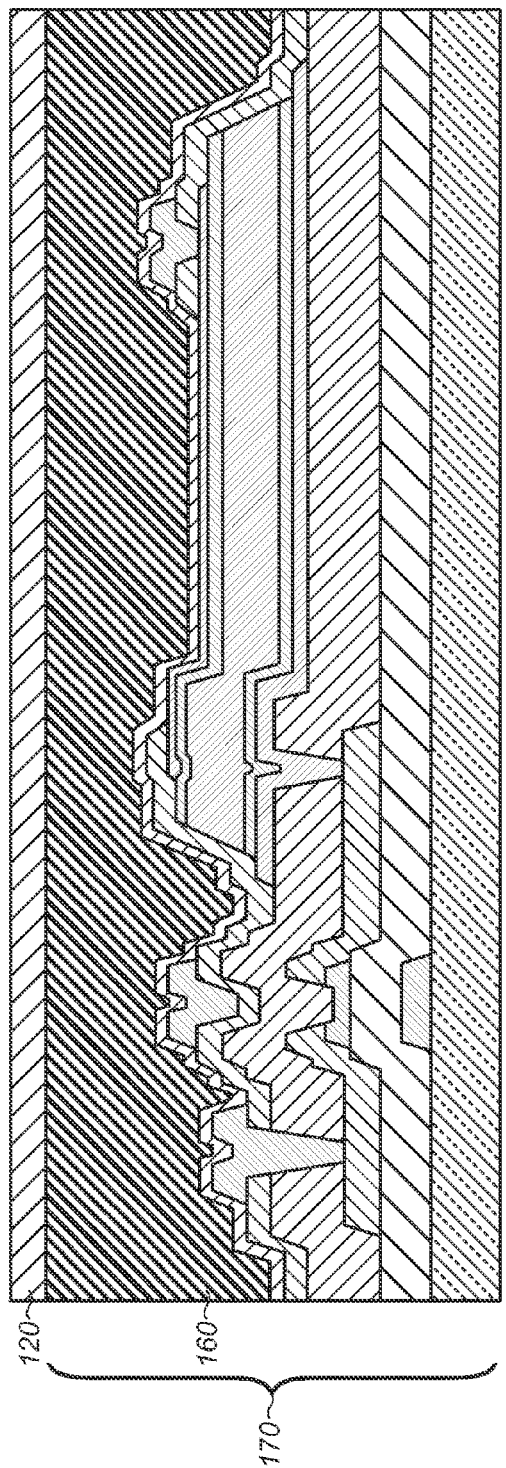
FIG. 13 is a diagram that shows a cross-section of a pixel of a digital radiographic (DR) array including an embodiment of an anti-static layer.

FIG. 13 is a diagram that shows a cross-section of a pixel of a digital radiographic (DR) array including an embodiment of an anti-static layer. As shown in FIG. 13, a low dielectric constant insulator 160 can be formed over an imaging array 170 and an anti-static layer 120 can be positioned on the side of the insulator 160 opposite the imaging array 170. The anti-static layer 120 can reduce or dissipate any charge residing on the surface of the insulator 160 and/or can reduce or prevent additional charge from forming. Since this charge can reside on the side of the insulating layer opposite the imaging array, the anti-static layer 120 can cause any surface charge to spread over the entire array rather than concentrating in at least one position. When handled in standard clean room conditions, which include a de-ionizing spray, or when connected to a grounding line or when connected to the ESD ground connection on the array, the surface charge over the imaging array 170 or insulator 120 can be significantly reduced by the anti-static layer 120.

As shown in FIG. 13, the low dielectric constant insulator 120 is coated over the imaging array 170 to provide physical and chemical protection to the imaging array 170. The additional insulator 160 is not required, but can be preferred because of the added protection provided to supplement the thin silicon nitride top-coat on the array.

Figure 14:
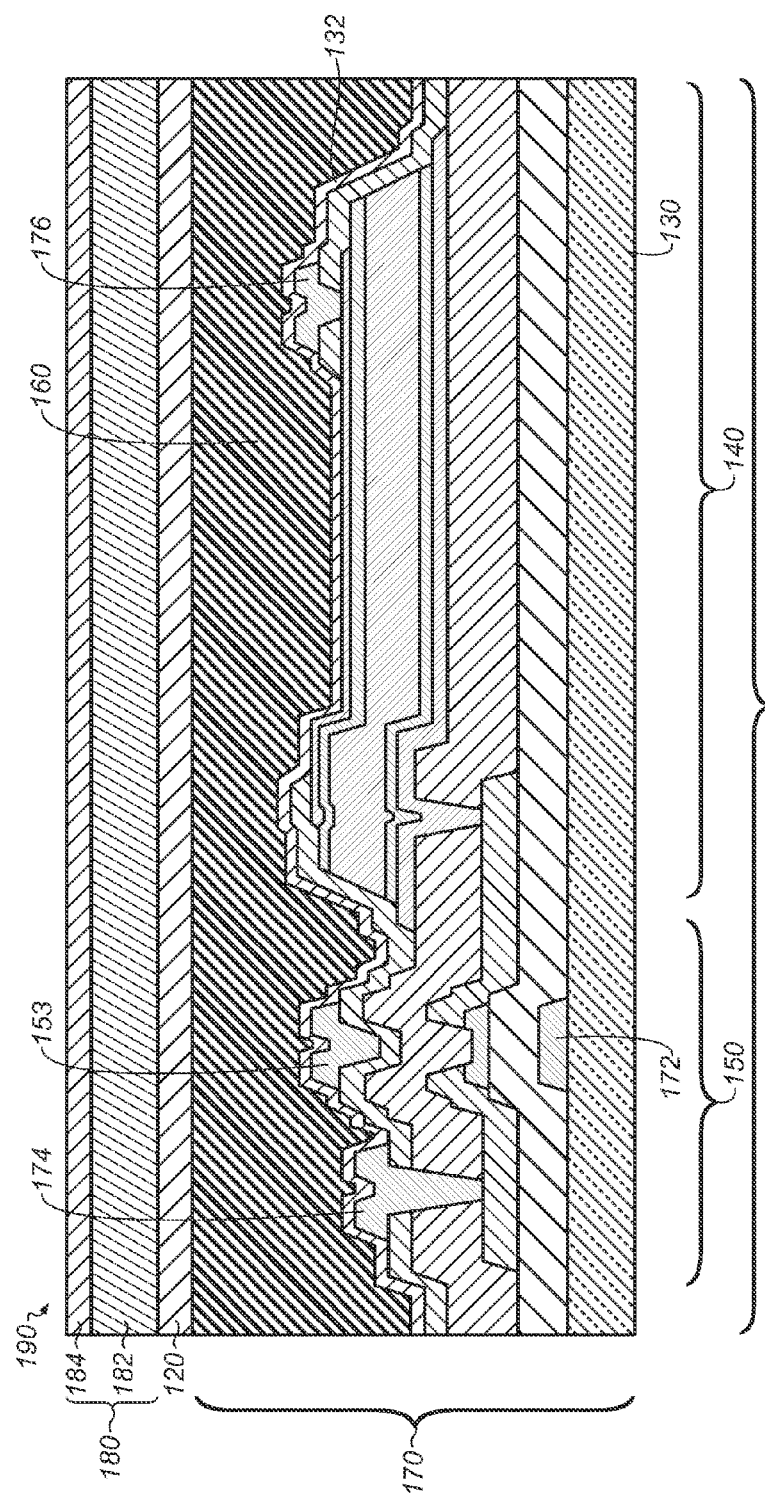
FIG. 14 is a diagram that shows a cross-section of another embodiment of a combined scintillator and radiographic imaging array.

FIG. 14 is a diagram that shows a cross-section of an embodiment of a radiographic detector configured to include a combined scintillator and imaging array using an anti-static layer in between. As shown in FIG. 14, an anti-static layer can dissipate charge residing on a surface of an imaging array (e.g., insulator) and/or can prevent or reduce additional charge from forming thereon.

In shown in FIG. 14, an imaging array 170 can include an array of pixels 100. As shown, pixels 100 can include known photosensing elements 140 (e.g., photosensors, n-i-p photodiodes, p-n junction photodiodes, MIS photosensors, phototransistors, etc.), known switching elements 150 (e.g., MOS thin-film-transistors, junction field-effect-transistors, fully-depleted SOI transistors, partially-depleted SOI transistors, silicon-on-glass transistors, bulk MOS transistors, bipolar transistors, etc.), or read-out circuits (not shown), etc. The photosensing elements 140 and the switching elements 150 can be substantially co-planar. The imaging array 170 can optionally include a passivation layer 132 (e.g., thin encapsulation layer) for protection and/or isolation of the imaging array 170. In the related art, a silicon nitride layer or a silicon dioxide layer, which have a high dielectric constant, can be used as the passivation layer 132, however, such passivation layers are thin and difficult to make thicker.

FIG. 14 shows an exemplary pixel of the imaging array 170 including a thin-film photosensor (e.g., PIN photodiode) and a TFT switch. Also shown in FIG. 14 is an optional low dielectric constant insulator 160 that can be formed (e.g., coated) over the imaging array 170 to provide a selected separation or fixed separation of the imaging array 170 from the scintillator 180. For example, the height of the low dielectric constant insulator 160 can be higher than the active surface of imaging array 170. Imaging array 170 can be formed on an insulating substrate 130 such as a glass substrate. Also shown in FIG. 14 is scintillating screen 182 that can include a substrate 184 (referred to herein as scintillator 180). The scintillator 180 can be a scintillating sheet pressed against the array, such as a sheet of Gd2O2S scintillating material, or deposited on the imaging array 170, such as evaporated CsI. The scintillator 180 can be placed over the low dielectric constant insulator 160 and the imaging array 170 to form an integrated digital radiography detector 190. Also shown in FIG. 14 are data lines 174, gate lines 172, metal lightshield 153 (e.g., for TFT switch 150), and bias lines 176. The bias line 176 can be coupled to an anode of photosensors or photodiodes.

As used herein, the active surface of imaging array 170 is intended to include the surface of the imaging array 170 that faces the scintillator 180 and comprises pixels 100. An active surface of imaging array 170 can include, for example, topography between the highest and lowest point of about 1 µm to over 3 µm.

The scintillator 180 can be applied in close proximity of the imaging array 170 in order to convert X-rays into visible light. The distance between scintillator and imaging array is generally made as small as possible to improve detector array characteristics (e.g., reduce optical crosstalk between adjacent pixels). However, the distance can be a tradeoff between capacitive loading of the scintillator on the imaging array and optical cross-talk.

Exemplary embodiments of anti-static layers (e.g., as shown in FIG. 14) can provide static protection between photodiodes and the scintillator and/or between TFTs and the scintillator. In cases where the scintillator is brought into contact with the imaging array 170, static charge can exist on the surface of the scintillator (e.g., scintillators are highly insulating). Surface static charge has been found in practice to have regions of surface electric field of both positive or negative $\gg 10$ kV/cm. In addition, any motion of the scintillator 180 against the imaging array 170 can generate charge due to tribo-electric charging. Such exemplary charges can be spread or distributed by the anti-static layer 120. Further, when the anti-static layer 120 is electrically connected either to a ground in the imaging array 170 (e.g., ESD ground) or to the external electronics, the charge can be reduced or removed from the anti-static layer.

Exemplary anti-static layers 120 can be formed with a variety of materials. Examples for materials for the anti-static layers 120 include but are not limited to conductive polymers, such as Clevious™ materials sold by Heraeus Corporation and nano-structured materials in an organic binder. Conductive polymers can include but are not limited to (a) sub-monolayer coverage for low conductivity or (b) thick coatings (e.g., 0.1 to 5 um) for higher conductivity, where the conductivity can depend on solids loading, material type and/or process conditions. Nano-structured materials in a binder (e.g., an organic binder) can include but are not limited to nano-rods that can have dimensions such as 1-30 nm cross-section and lengths from microns to millimeters, silver nanowires, or carbon nanotubes.

Certain exemplary embodiments of anti-static layers can instantiate various preferred properties, individually or in combination, including but are not limited to thickness, resistivity, optical transmission, optical index of refraction, and/or dielectric constant.

A thickness of anti-static layer embodiments can be a trade-off between optical cross-talk between pixels and required conductivity. A thick layer (e.g., greater than 5 um) can allow optical cross-talk, for example when combined with additional transparent layers between the imaging array and the absorptive or scattering region of the scintillator. These additional transparent layers can include organic and inorganic dielectrics over the imaging array and clear coating layers over a scintillator sheet. However, as the anti-static layer is thinned, its conductivity can be diminished, resulting in reduced anti-static protection. For certain antistatic layer embodiments, a layer thickness of less than 5 um is desired and a layer thickness less than 2 um is preferred.

A resistivity of anti-static layer embodiments can be a trade-off between electrical effect on the imaging array and anti-static protection. A low resistivity (e.g., less than $1 \times 10^4$ ohms per square) can add to the data-line capacitance, thereby increasing imager (e.g., integrated digital radiography detector 190) noise, and to the photodiode capacitance, thereby increasing the charge transfer time constant between photo-sensor (e.g., photodiode) and dataline. A high resistivity (e.g., greater than $1 \times 10^{10}$ ohms per square) can result in a long time constant for discharge of static electricity.

An optical transmission of anti-static layer embodiments is preferably a high optical transmission (e.g., greater than 90%, 95%) over the visible spectrum (e.g., >90% over 400 nm to 700 nm wavelengths) for clinically acceptable or maximum quantum efficiency.

An optical index of refraction for anti-static layer embodiments can be intermediate between the scintillator and the silicon nitride top coat of the imaging array to reduce or minimize reflection losses at the anti-static layer. In exemplary embodiments where an organic encapsulation layer is disposed between the imaging array and the anti-static coating, matching the indices of each of the optical layers or an intermediate optical index of refraction is desired.

Certain exemplary embodiments of radiographic imaging arrays can further include provision of a reference voltage or ground connection for anti-static film/layer embodiments over a radiographic imaging rarity. As described herein, anti-static layer embodiments for radiographic arrays alone can cause charge to spread over the entire surface of the anti-static layer (e.g., imaging array), which is preferred to the concentrations of positive and of negative charge that can form on insulators and cause mura, or non-uniformity of parameters such as dark current or image lag in the array. Further, exemplary embodiments can provide a reference voltage or a ground connection to an anti-static layer can reduce or prevent uniform charge buildup on the anti-static material.

Various exemplary ground connection (e.g., reference voltage) embodiments for anti-static layers 120 include but are not limited to (a) provision of contact pads for the anti-stat coating on the imaging array or (b) contacts can be provided within the imaging array (e.g., internal to each pixel or in a sparse matrix within the imaging array). Exemplary ground connection (e.g., reference voltage) embodiments provision of contact pads for the anti-stat coating on the imaging array can include (i) electrical connection to a separate electrical lead to the external electronics, (ii) electrical connection to the ESD ground trace on the array, and/or (iii) electrical connection to one of the voltage or bias connections on the imaging array 170, such as the bias for the photodiode.

Figure 15:
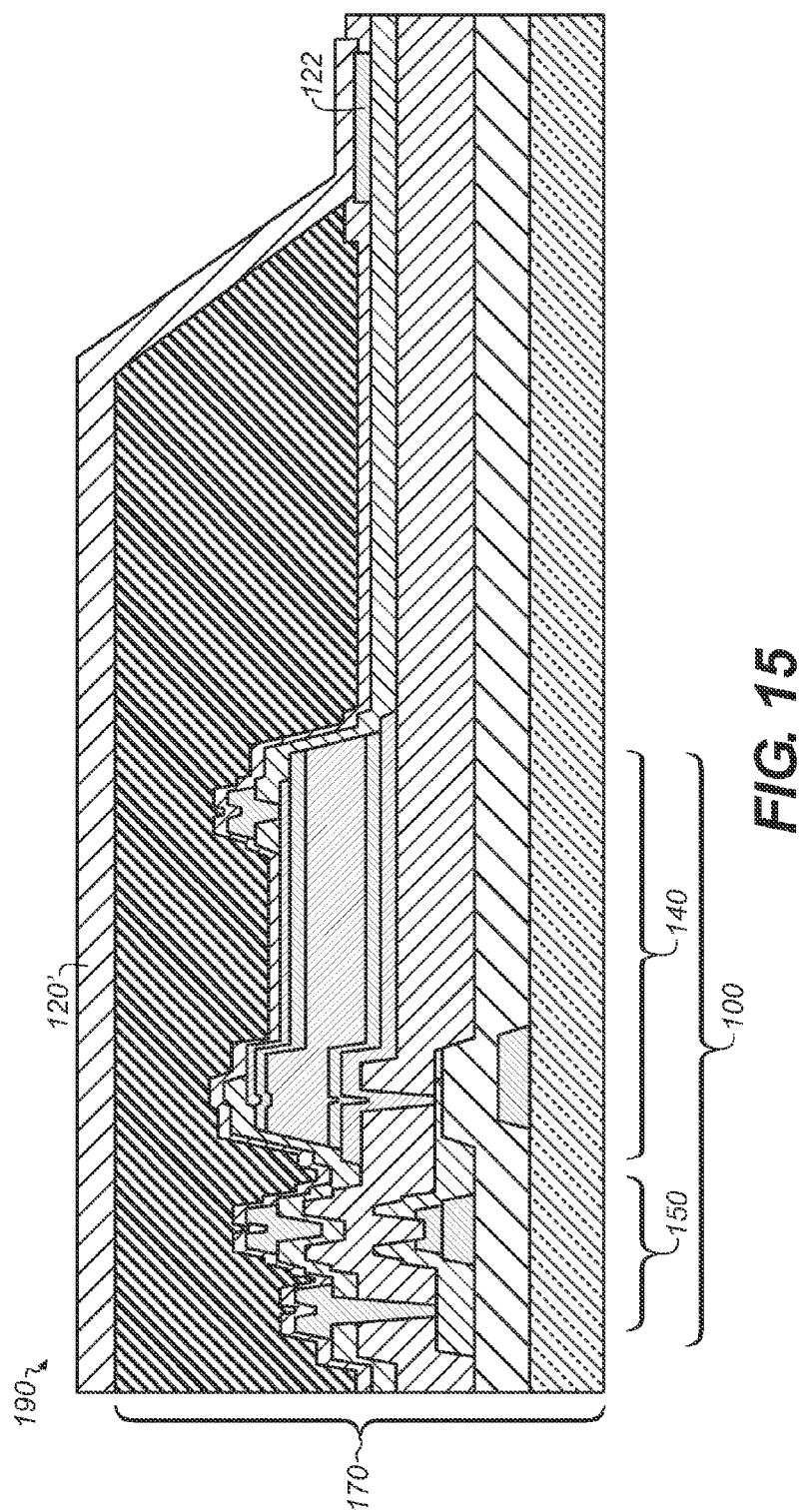
FIG. 15 is a diagram that shows a cross-section of another embodiment of a radiographic detector configured to include an imaging array with an electrically coupled anti-static layer thereover.

FIG. 15 is a diagram that shows a cross-section of an embodiment of a radiographic detector configured to include an imaging array with a grounded anti-static layer thereover. As shown in FIG. 15, a contact can be provided around an imaging array perimeter for an anti-static coating. In one embodiment, contact pads 122 can be provided external to the imaging portion of the imaging array 170 positioned at one or multiple locations around the perimeter of the integrated digital radiography detector 190 to reduce or minimize series resistance of a grounded anti-static layer 120'. An area of the contact pads 122 can be chosen sufficiently large that the contact series resistance contributes insignificantly or minimally to the sheet resistance of the anti-static layer.

Figure 16:
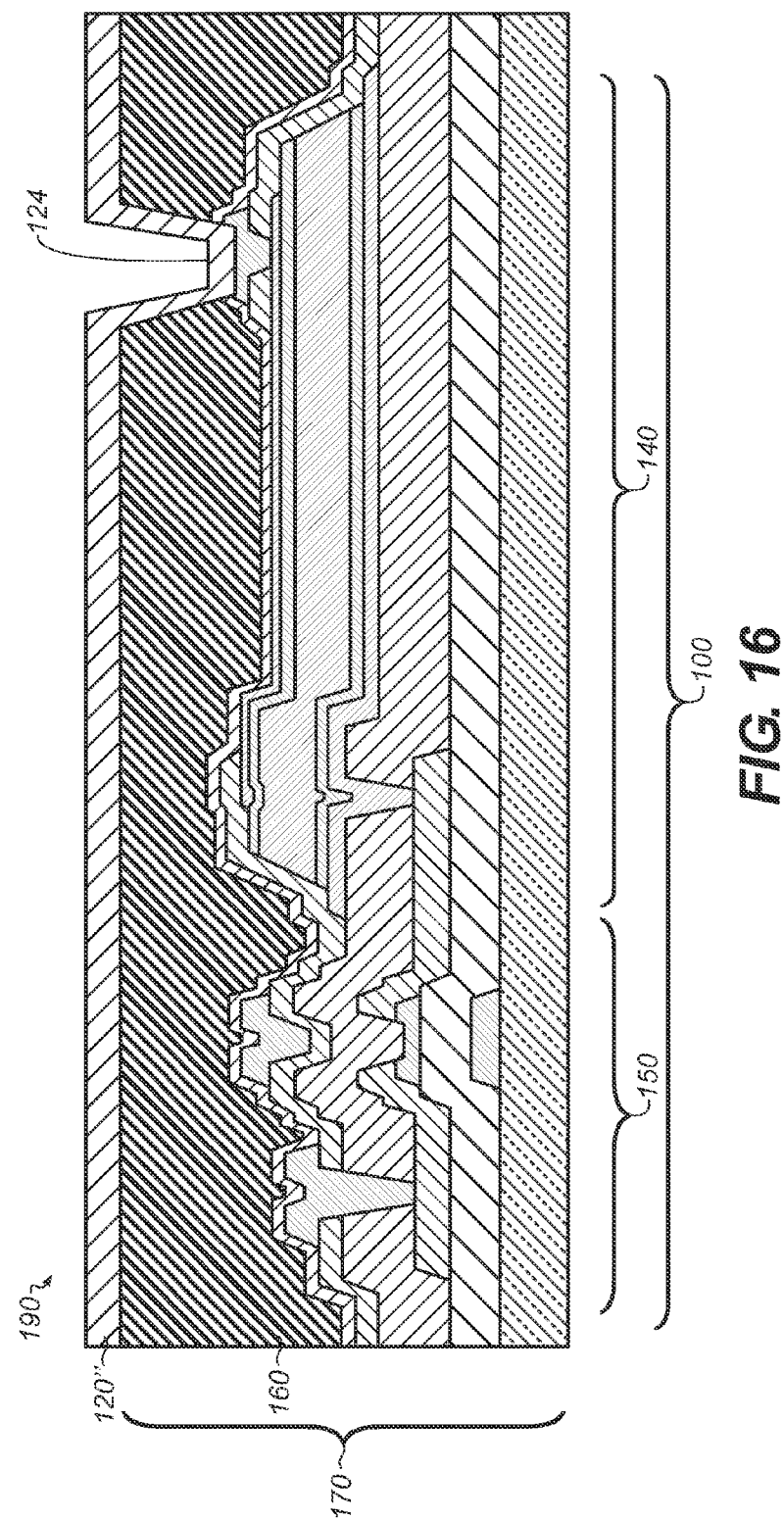
FIG. 16 is a diagram that shows a cross-section of another embodiment of a radiographic detector configured to include an imaging array with an electrically coupled anti-static layer thereover.

FIG. 16 is a diagram that shows a cross-section of another embodiment of a radiographic detector configured to include an imaging array with an anti-static layer thereover that is coupled to a reference voltage. As shown in FIG. 16, a contact can be provided internal to the pixel 100 using the bias line 176 in the imaging array 170 through via 124 in the encapsulation layer 160 and top nitride layer 132. Preferably without additional modification to the imaging array 170, the bias line 176 can be connected to an external bias supply in the integrated digital radiography detector 190 to provide a reference voltage (e.g., ground) to the anti-static layer 120".

Additional alternate embodiments for electrical connection of anti-static layers can use conductive traces in the radiographic imaging array to provide a reference voltage (e.g., ground reference) to the anti-static layers. For example, electrical grounding for the anti-static layers 120, 120', 120" can use (a) separate metal traces for anti-static connection within the array and vias between these metal traces and the anti-static layer and/or (b) provide a sparse matrix of connections to the anti-static layer in the imaging array positioned between a limited number of pixels (e.g., such as every 256 rows or 256 columns, at selected prescribed locations, aperiodic, etc.).

Alternate embodiments for electrical connection of anti-static layers can use physical contact(s) or electrical coupling provided through a conductive coating or an anti-static coating on the scintillator, preferably where the scintillator anti-static coating is attached or electrically connected to a reference voltage or ground connection.

Figure 17:
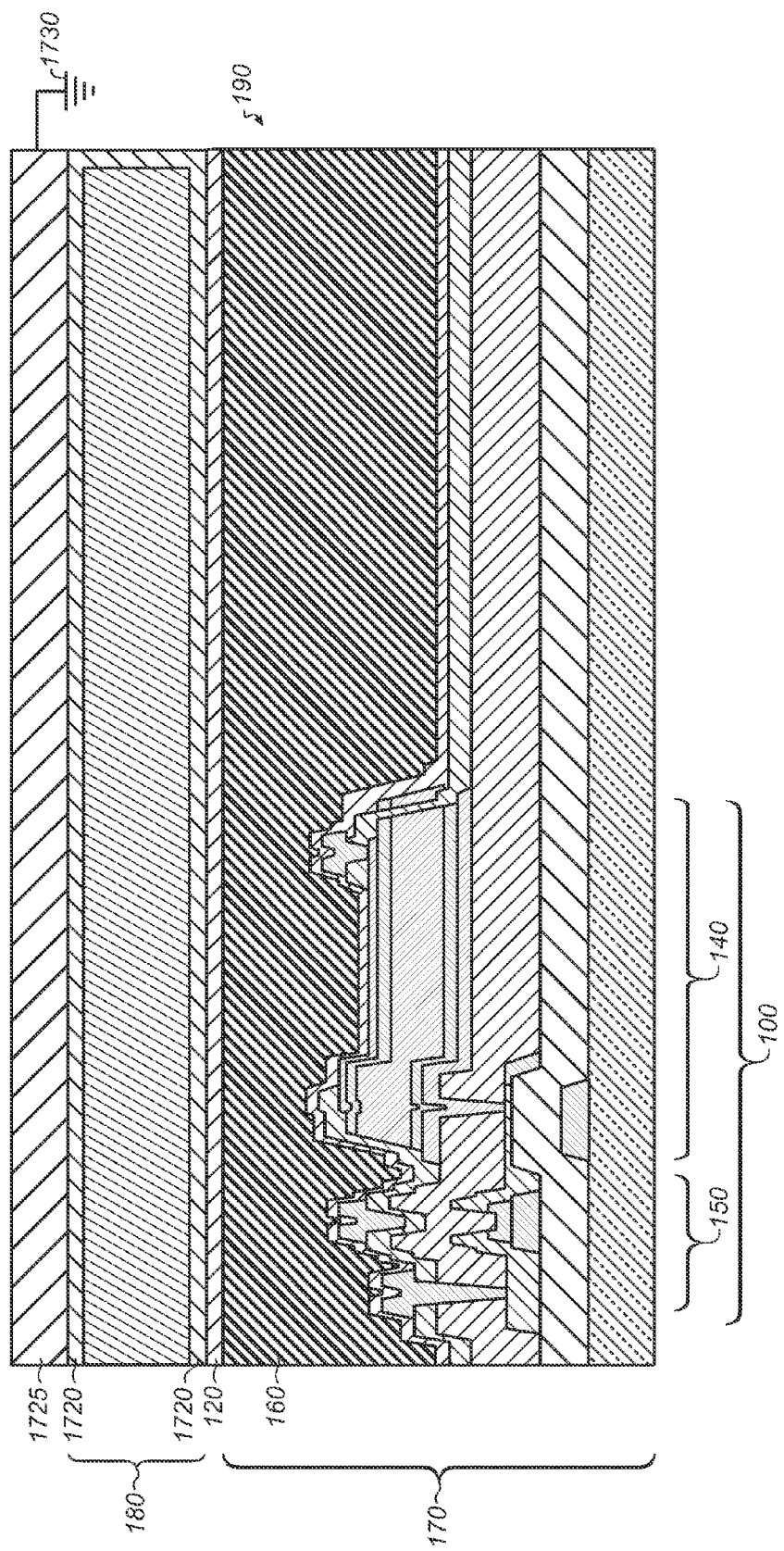
FIG. 17 is a diagram that shows a cross-section of another embodiment of a radiographic detector configured to include an imaging array with an electrically coupled anti-static layer thereover.

FIG. 17 is a diagram that shows a cross-section of another embodiment of a radiographic detector configured to include a combined scintillator and imaging array with an anti-static layer therebetween that is coupled to a reference voltage (e.g., ground). As shown in FIG. 17, a contact can be provided through a cassette or housing of the digital detector, which is typically conductive. Preferably without additional modification to the imaging array 170, the anti-static layer 120 can be connected (e.g., physically, electrically) to an anti-static layer 1720 of the scintillator 180 that can be connected to a cassette 1725 of the radiographic detector that can be connected to provide a reference voltage 1730 (e.g., ground) to the anti-static layer 120.

Figure 18:
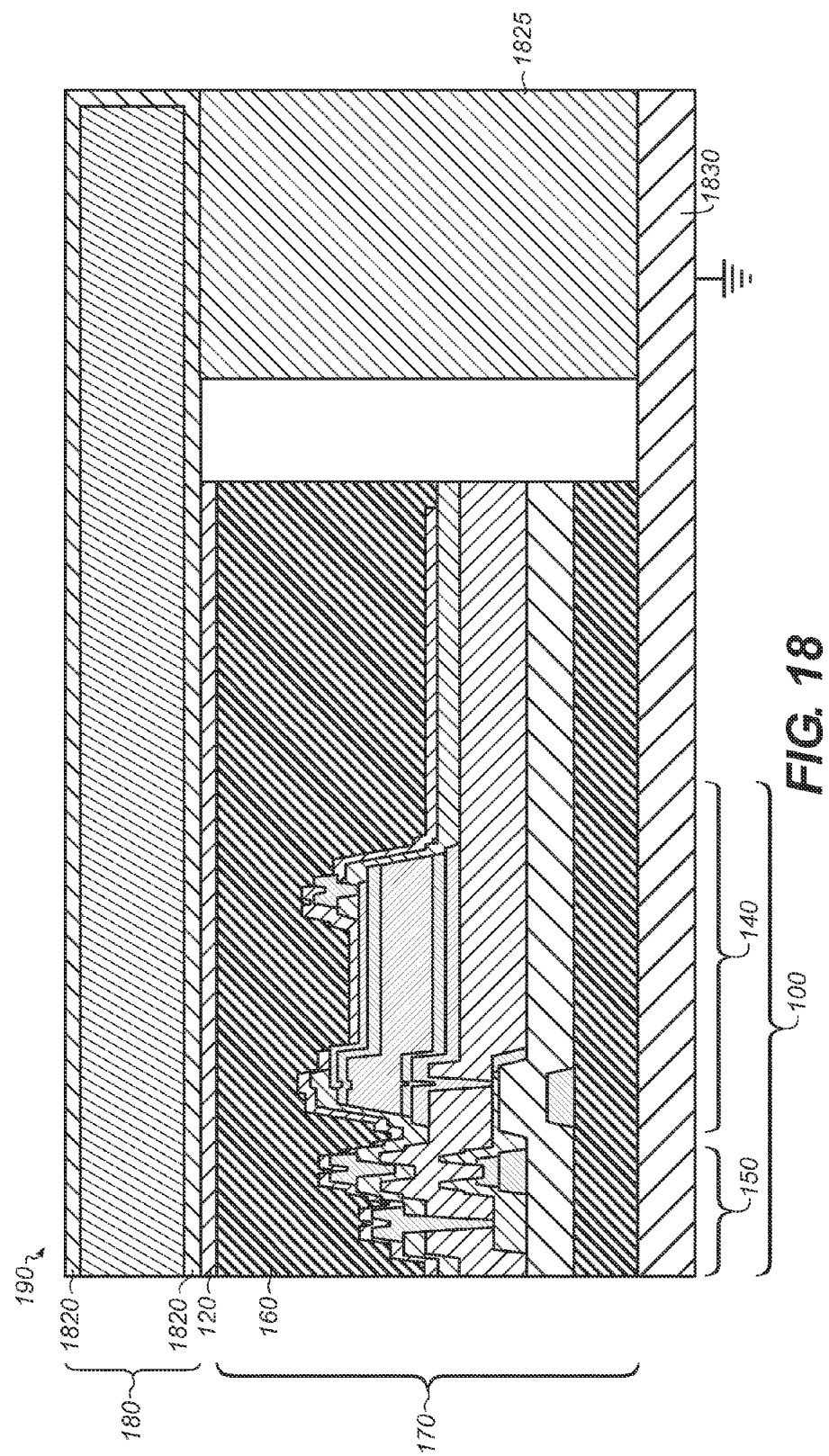
FIG. 18 is a diagram that shows a cross-section of another embodiment of a radiographic detector configured to include an imaging array with an electrically coupled anti-static layer thereover.

FIG. 18 is a diagram that shows a cross-section of another embodiment of a radiographic detector configured to include a combined scintillator and imaging array with an anti-static layer therebetween that is coupled to a reference voltage. As shown in FIG. 18, a contact can be provided through a metal or conductive contact to a surface of the scintillator disposed closest to the imaging array 170. For example, the scintillator 180 can be coated on at least the side proximate to the imaging array 170 with an anti-static coating 1820, and within the housing of the radiographic detector, a conductor such as a conductive gasket 1825 can be provided to allow electrical contact between a mounting plate 1830 and the anti-static coating 120 using the anti-static coating 1820 on the scintillator sheet.

Figure 19:
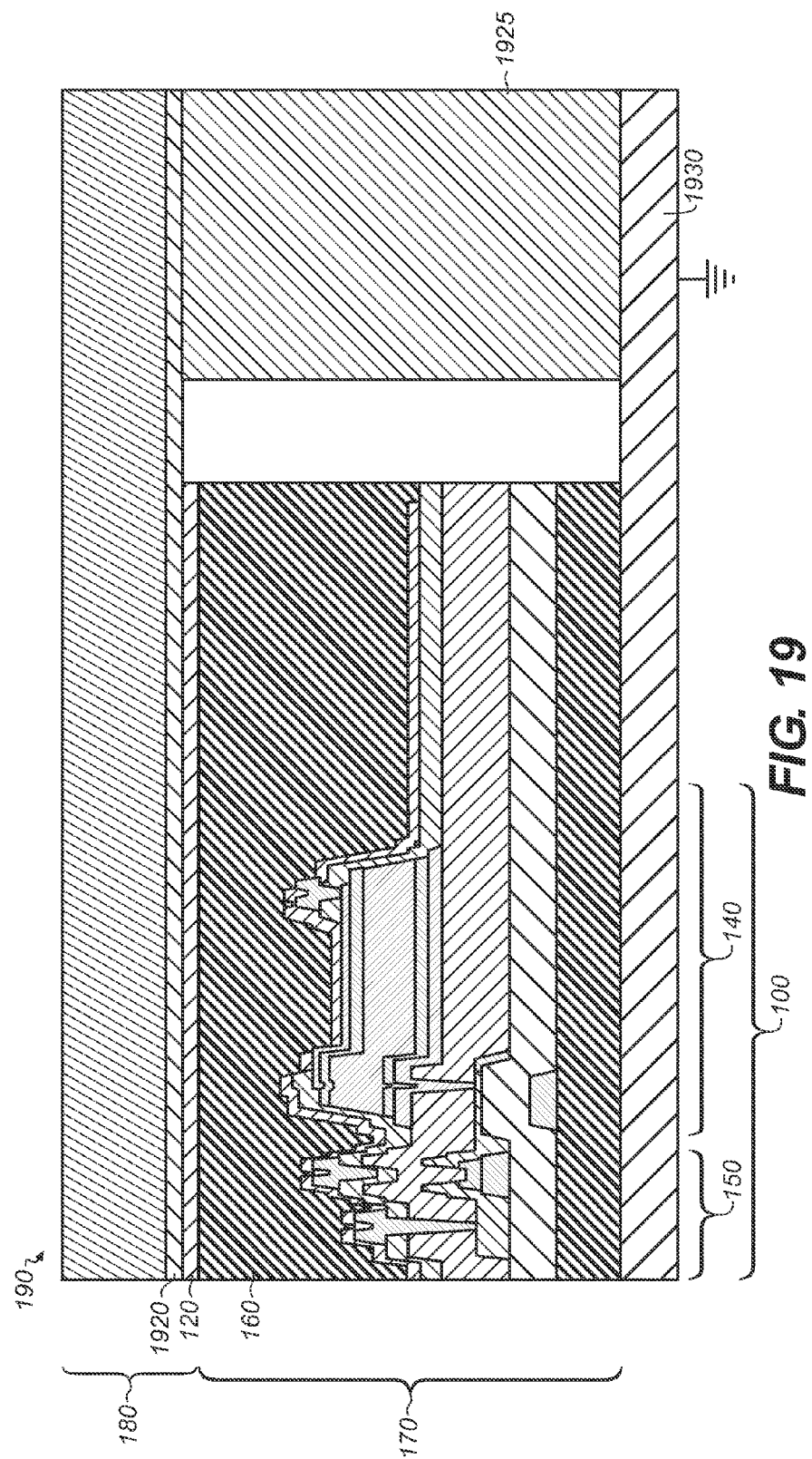
FIGS. 19-20 are diagrams that show cross-sections of additional embodiments of a radiographic detector configured to include a combined scintillator and imaging array with an anti-static layer therebetween that can be coupled to a reference voltage.
Figure 20:
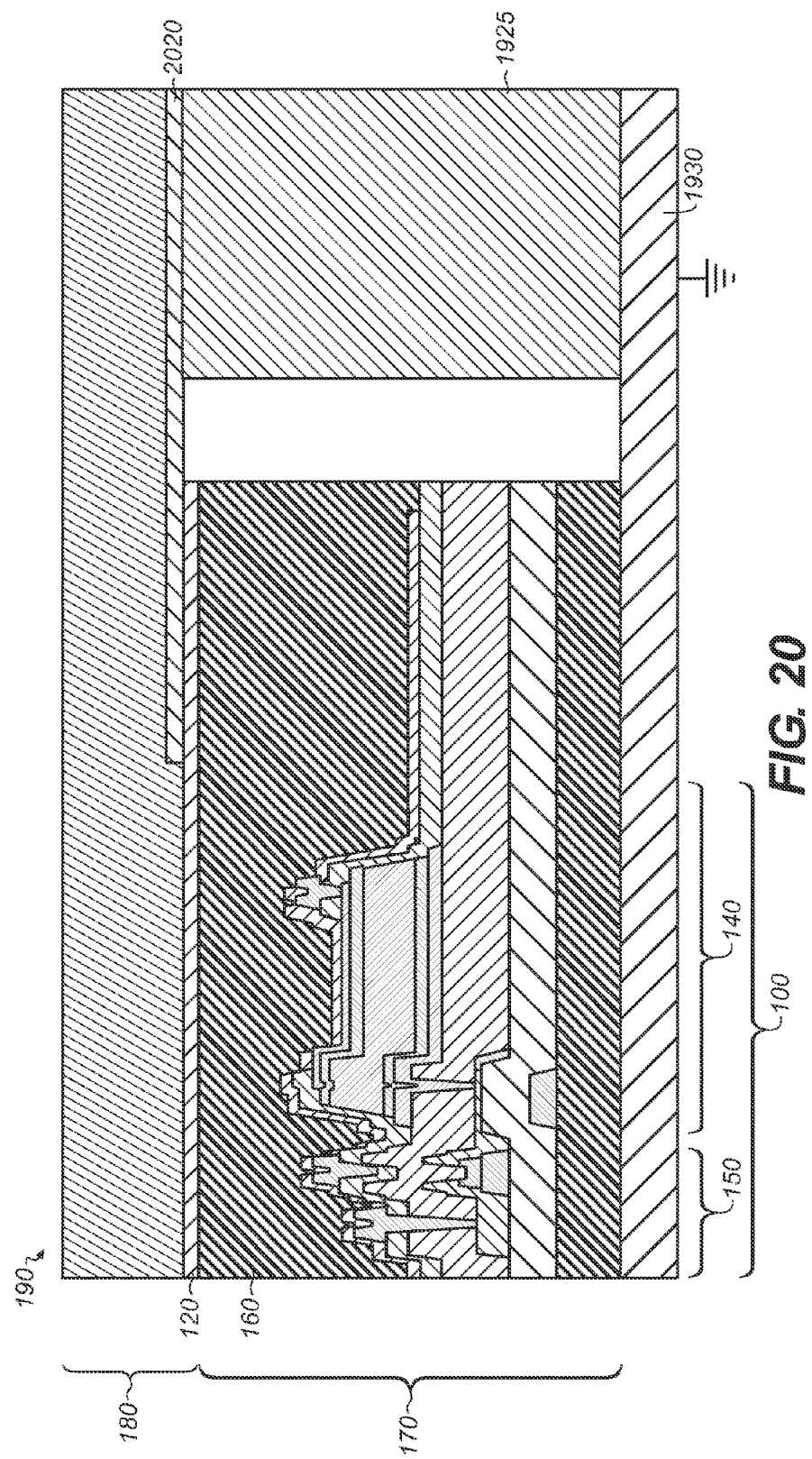

FIGS. 19-20 are diagrams that show cross-sections of additional embodiments of a radiographic detector configured to include a combined scintillator and imaging array with an anti-static layer therebetween that can be coupled to a reference voltage. As shown in FIG. 19, narrow metal or conductive traces 1920 can be patterned on the scintillator sheet and can extend across a lower surface of the scintillator 180 and be connected to the anti-static layer 120. As shown in FIG. 20, conductive traces 2020 can be patterned on the scintillator 180 around the perimeter of the imaging area of the imaging array 170. The anti-static layer 120 can be coupled or electrically connected through the conductive traces 1920 or the conductive traces 2020 (e.g., using conductive gasket 1925) to a reference voltage such as but not limited to mounting plate 1930. Exemplary embodiments of conductive traces can include high transparency to light emitted by the scintillator, opaque and/or an index of refraction corresponding to the imaging array/scintillator. Embodiments of radiographic detector arrays 190 can reduce problems caused by noise generated by interactions between the scintillator 180 and elements in the imaging array 170. By reducing noise caused by the scintillator 180 in relation to the imaging array 170, embodiments of radiographic digital detector arrays 190 can include improved imaging characteristics.

As will be obvious to one of ordinary skill in the art, the various embodiments can be combined to form many different combinations, all of which are intended to be incorporated by this disclosure. In one embodiment, exemplary scintillator 180 and/or imaging array 170 can be coated with additional optional layers (e.g., a protective layer). As will be obvious to one of ordinary skill in the art, the various embodiments can be combined to form many different combinations, all of which are intended to be incorporated by this disclosure.

FIG. 14 is a diagram that shows a cross-section of an embodiment of a radiographic detector configured to include a combined scintillator and imaging array using a continuous anti-static layer in between. As shown in FIG. 14, an anti-static layer can dissipate charge residing on a surface of an imaging array (e.g., insulator) and/or can prevent or reduce additional charge from forming thereon.

FIG. 15 is a diagram that shows a cross-section of an embodiment of a radiographic detector configured to include an imaging array with a continuous grounded anti-static layer thereover.

There are various disadvantages to the continuous anti-static layer such as illustrated in FIG. 14 and FIG. 15. For example, various disadvantages include anti-static layers can capacitively couple to the dataline, which can result in an increase the dataline capacitance and an increase in imaging array noise. Further, the ant-static layer can capacitively couple to the anode of the photosensor, thereby increasing the time constant for charge transfer from the photosensor/photodiode to the dataline ($\tau = R_{TFT} C_{PD}$ where $\tau$ is the time constant, $R_{TFT}$ is the TFT on-resistance and $C_{PD}$ is the diode capacitance).

In addition, there are several short-comings of existing arrays that can be addressed or remedied by anti-static layers containing colorant. For example, a conductive or metal light-shield over the TFT, conventionally included in related art radiographic imaging arrays, adds capacitance to the imaging array including the dataline and/or the gateline. As described herein, this lightshield can be replaced with a patterned anti-static coating with colorant added. Further, there are areas of the pixel in which there are no light-blocking layers between the scintillator and the substrate. Light from the scintillator can penetrate into the substrate in such areas to cause image flare and/or reduced resolution. An antistatic layer with colorant can reduce or prevent such light penetration.

Certain exemplary embodiments can provide a patterned anti-static layer for use with a radiographic imaging array for a digital radiographic detector. Several embodiments are described for the location of the patterned anti-static coating at the pixel and array level. In addition, several additional embodiments are described in which colorant can be added to the anti-static material to address or improve other array characteristics.

Figure 21:
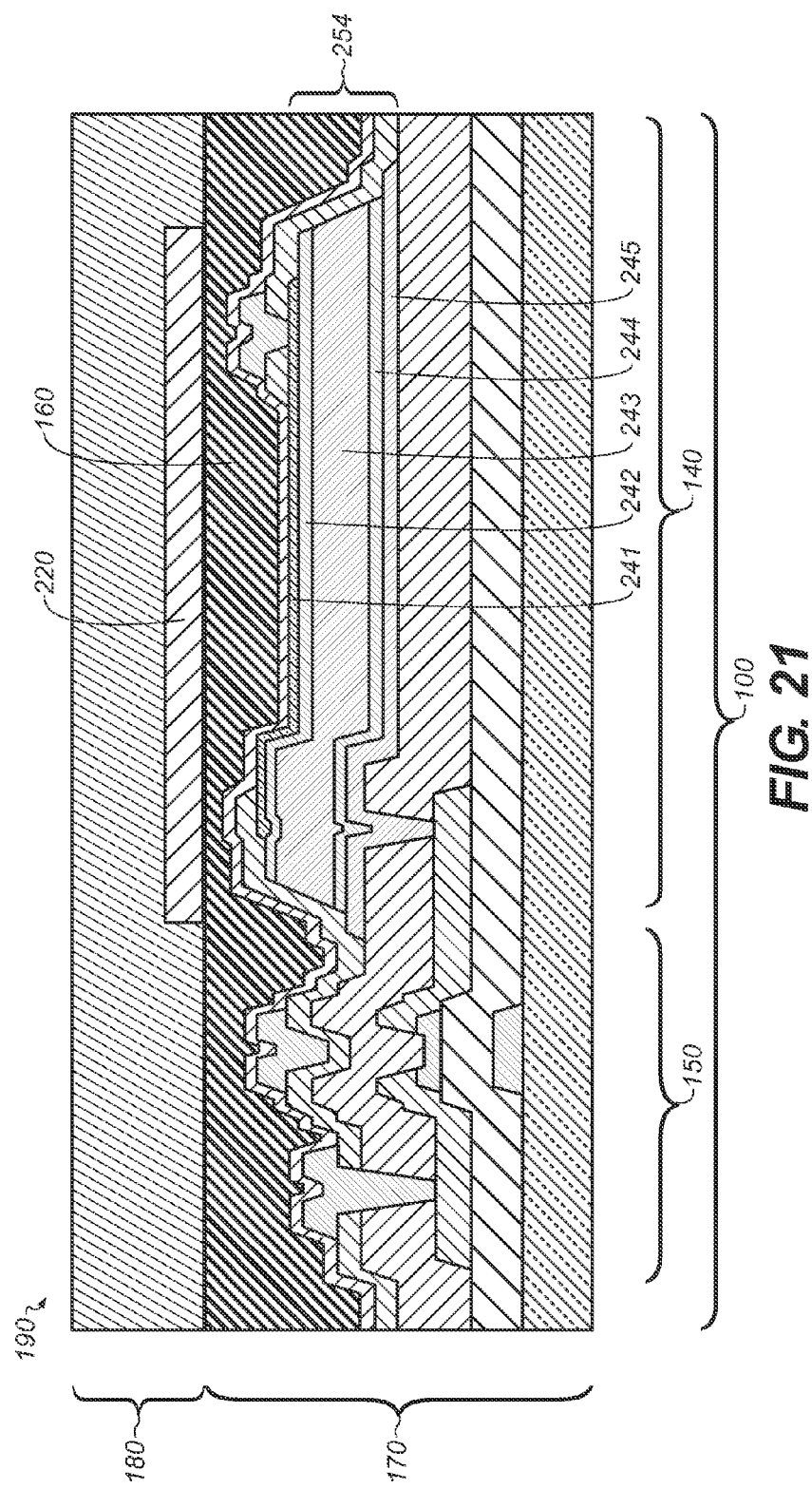
FIG. 21 is a diagram that shows a cross-section of a radiographic detector configured to include an imaging array with a patterned anti-static layer embodiment thereover.

FIG. 21 is a diagram that shows a cross-section of a radiographic detector configured to include an imaging array with a patterned anti-static layer embodiment thereover. A large amount of surface charge can cause permanent damage to photodiode 254. As shown in FIG. 21, a patterned anti-static layer 220 can be patterned to remain over the photodiode 254, but not over datalines of the pixels 100. The photodiode 254 can be the most static-sensitive component in the imaging array 170. A small amount of surface charge can act on the sidewall of a mesa photodiode 254, to cause an increase in sidewall leakage, increased image lag caused by surface trapping of electrons or holes, and/or an increase in low-frequency (e.g., flicker) noise in the photodiode 254. By patterning the anti-static layer 220 over the photodiode 254, there is little or no increase in dataline capacitance because the anti-static layer 220 and the dataline are not proximate. Thus, the embodiment shown in FIG. 21 can implement a radiographic imaging array with the advantages of static protection of the photodiodes without disadvantages of increased dataline thermal noise. As shown in FIG. 21, the photodiode 254 can include a transparent electrode contact (e.g., to p+ a-Si) 241, a p+ amorphous silicon (a-Si) layer 242, an intrinsic a-Si layer 243, a n+ a-Si layer 244, and a metal electrode 245 (e.g., pixel electrode contact to n+ a-Si.

Figure 22:
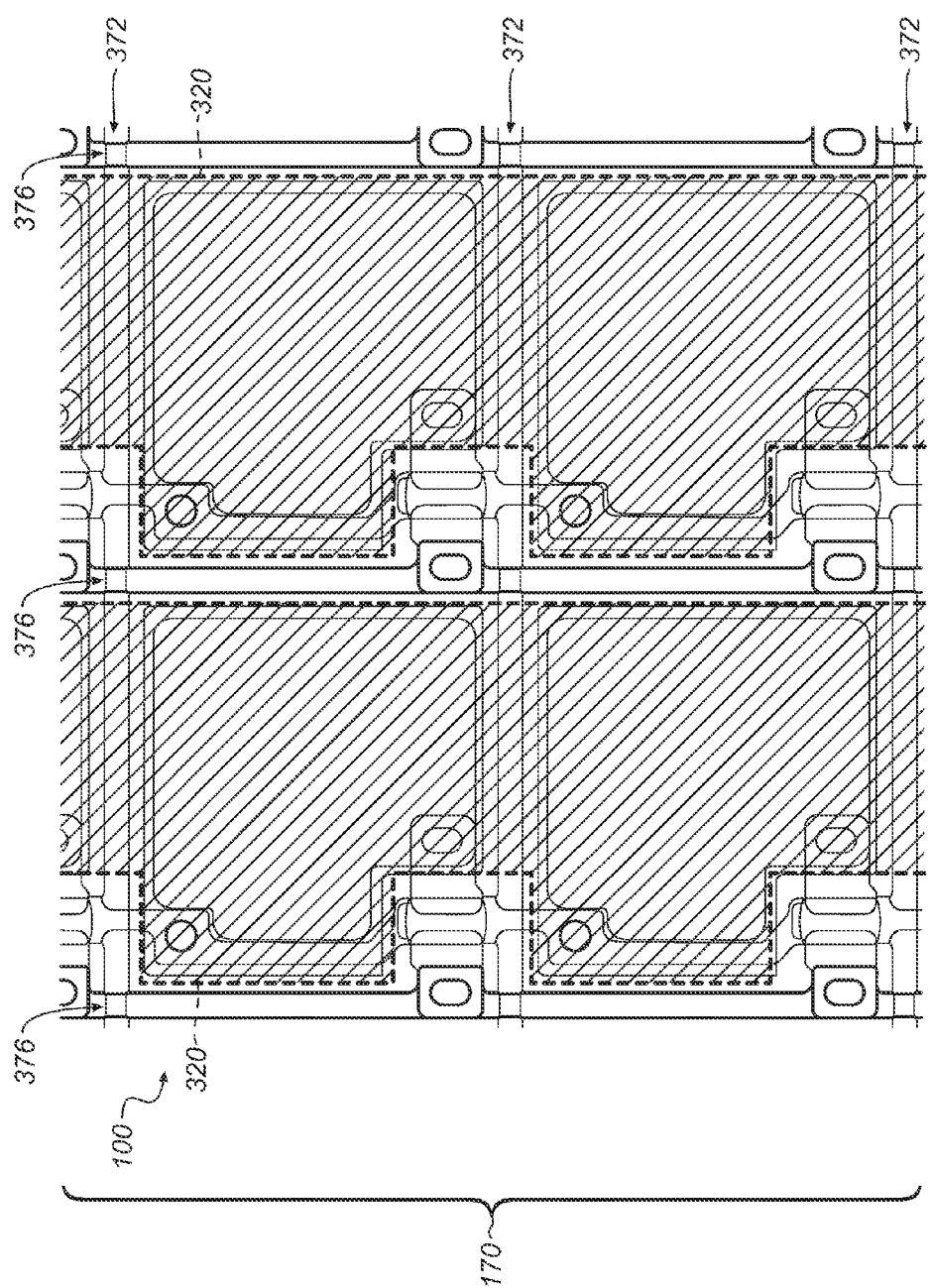
FIGS. 22-24 are diagrams that show a top-down view of a layout for additional exemplary embodiments of a radiographic detector configured to include an imaging array with a patterned anti-static layer thereover.
Figure 23:
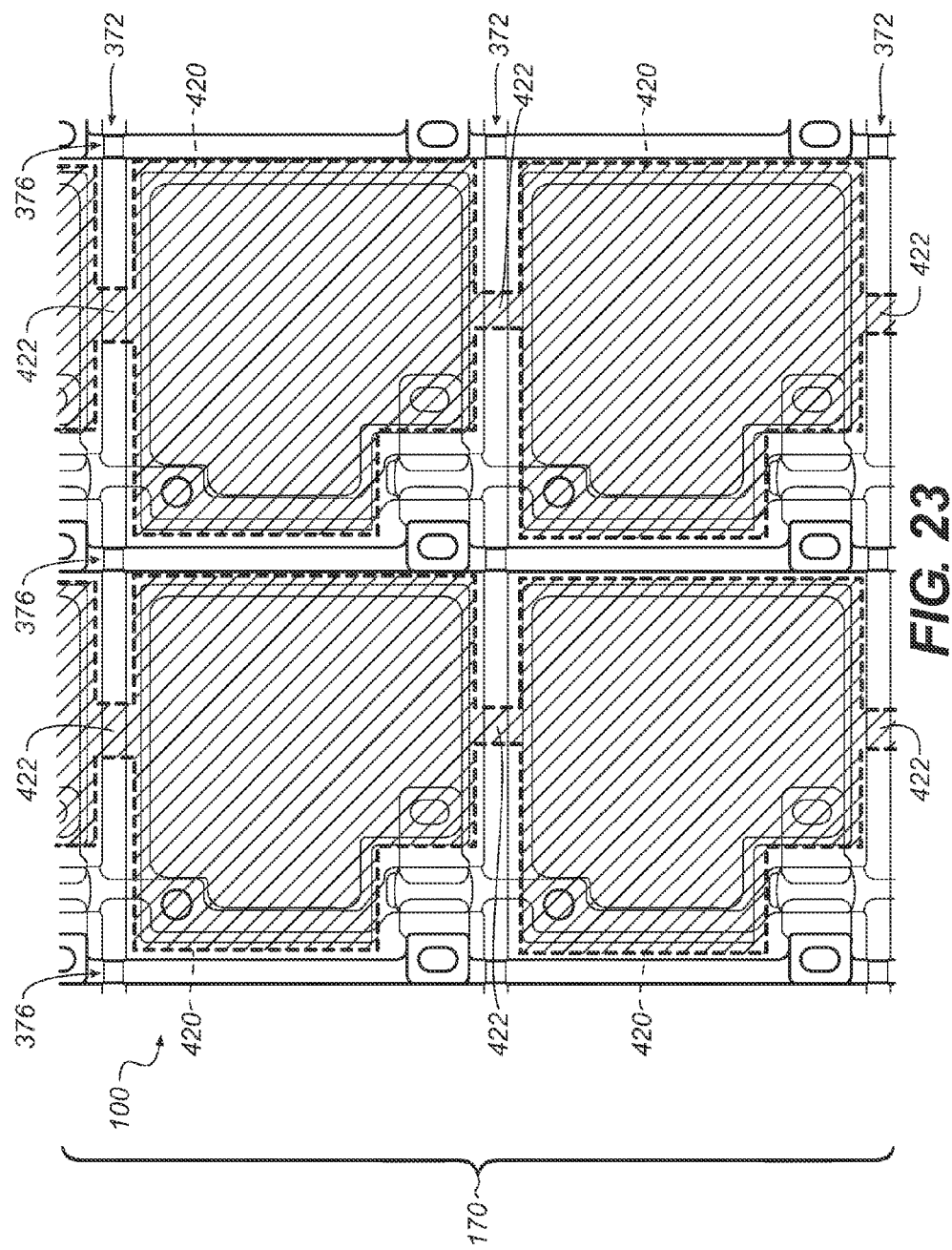
Figure 24:
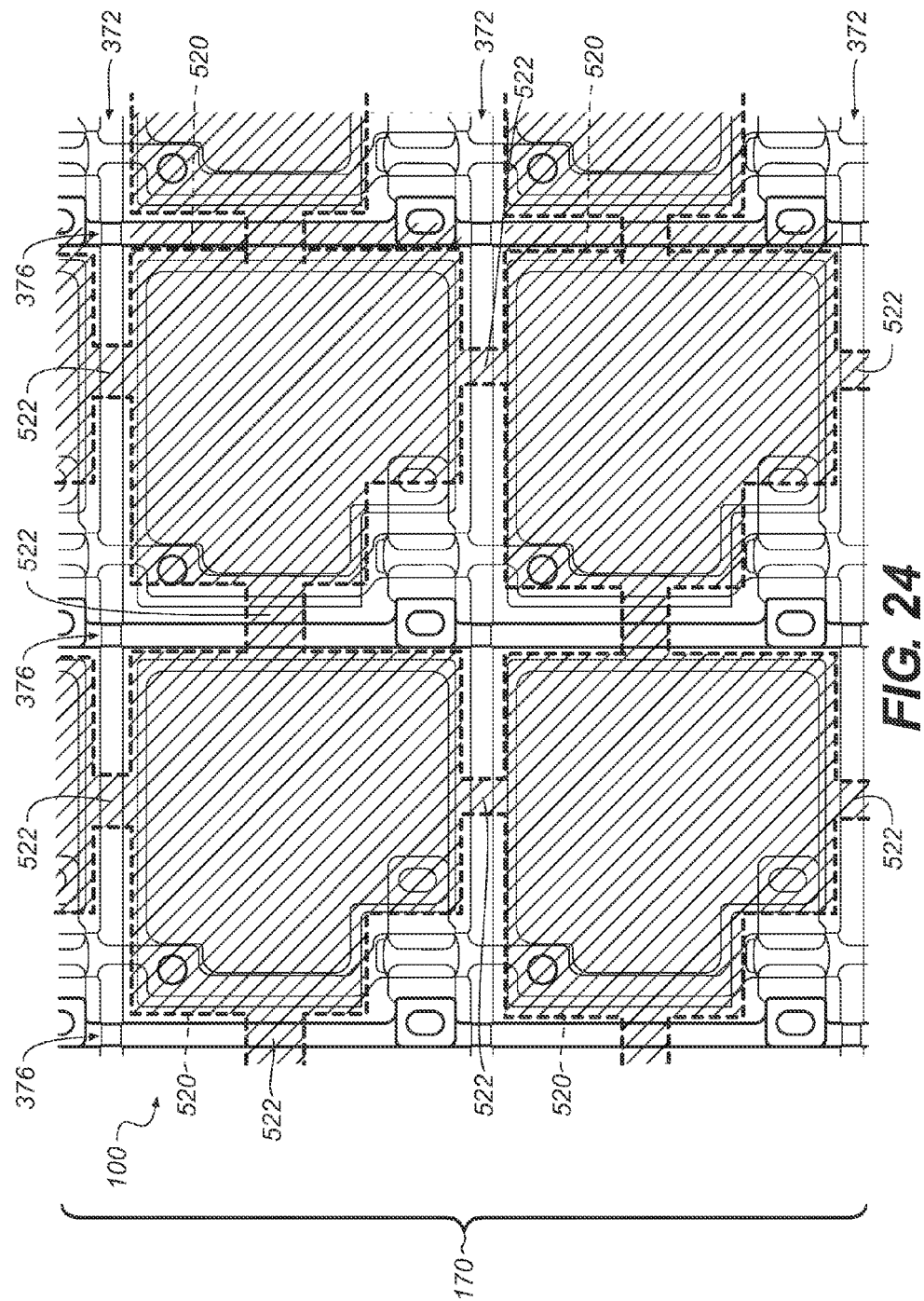

There are various alternatives for embodiments of patterned anti-static layers as shown in FIG. 21. FIGS. 22-24 are diagrams that show exemplary embodiments of a radiographic detector configured to include an imaging array with a patterned anti-static layer thereover. As shown in FIG. 22, a first alternative layout for a patterned anti-static coating 320 does not overlie the dataline 376 and can be oriented continuously along columns of the imaging array 170. The layout for the patterned anti-static layer 320 advantageously can greatly reduce capacitive loading of the dataline 376 while still providing protection against static charge to the photodiodes 254. However, the resistance of the antistatic columns becomes quite high because of the number of squares of sheet resistance. The number of squares of sheet resistance of a column can be equal to the number of pixels in the column, for example, greater than 1000. The large number of squares of sheet resistance can result in a reduction in the ability of the anti-static coating to dissipate charge rapidly. Further, the switching voltages applied to the gatelines during readout can couple capacitively to the anti-static coating 320, which can result in potential voltage transients in the vicinity of the switched dataline 376.

FIG. 23 is a diagram that shows a patterned anti-static coating 420 embodiment including a second alternative layout that does not overlie the dataline 376 and can be oriented continuously along columns of the imaging array 170. As shown in FIG. 23, the anti-static coating 420 can be patterned to reduce or minimize an overlap area 422 over the gate lines 372, which can reduce any capacitive coupling with the gate lines 372, and therefore reduce any transient during gate-line clocking. However, a series resistance of the patterned anti-static coating 420 is increased.

FIG. 24 is a diagram that shows a third alternative layout for a patterned anti-static coating 520 embodiment that can be oriented continuously along rows and columns of the imaging array 170. As shown in FIG. 24, the anti-static coating 520 can be patterned to reduce or minimize a crossover area 522 with both data line 376 and with gate line 372. However, because the interconnection of the anti-static layer 520 can be in the form of a grid, the net resistance from the perimeter contacts to the anti-static coating 520 and any pixel 100 in the imaging array 170 can be substantially less than the embodiments of FIG. 22 or FIG. 23.

Figure 25:
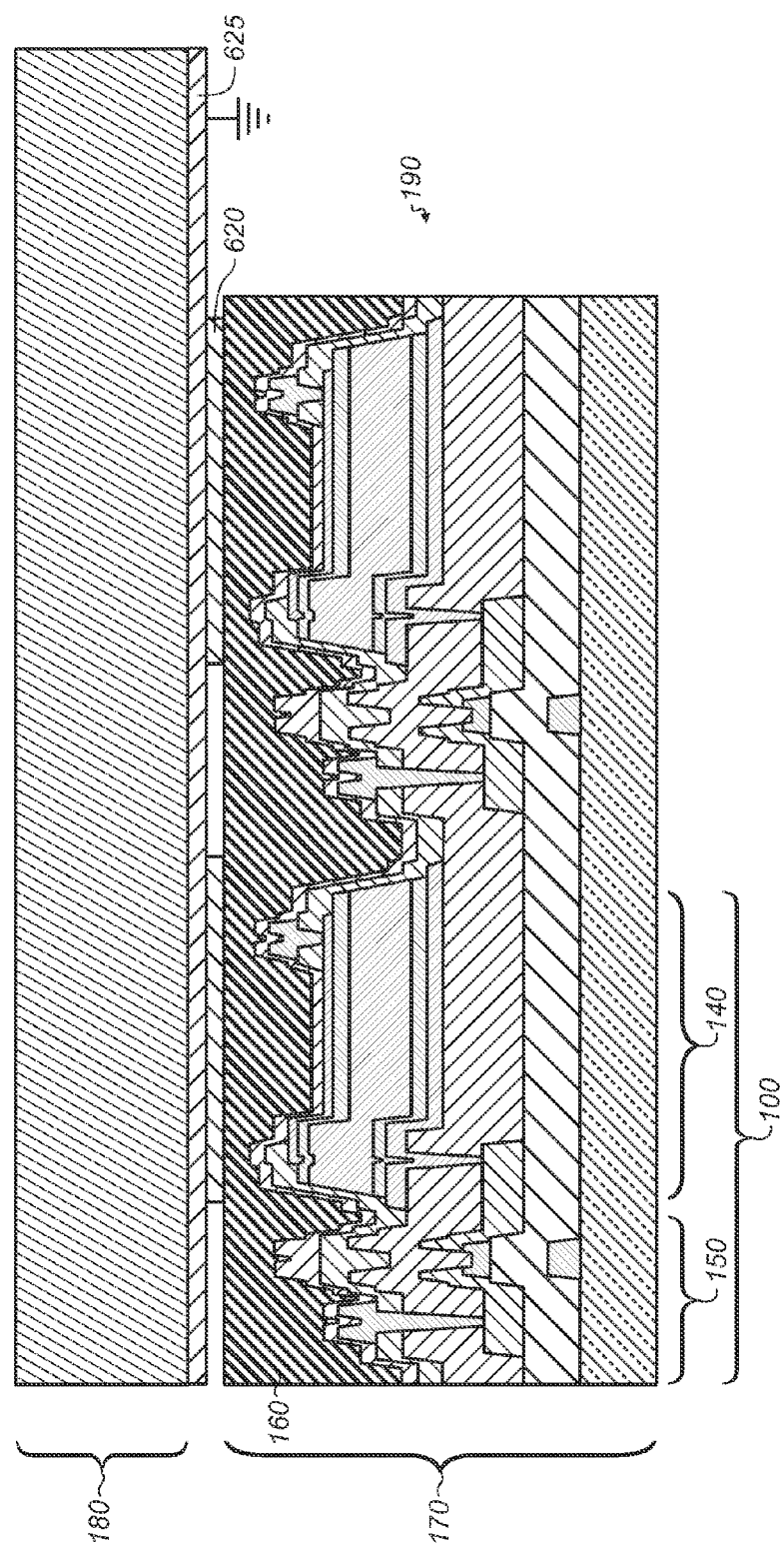
FIG. 25 is a diagram that shows a cross-section of another embodiment of a radiographic detector configured to include an imaging array with a patterned anti-static layer thereover.
Figure 26:
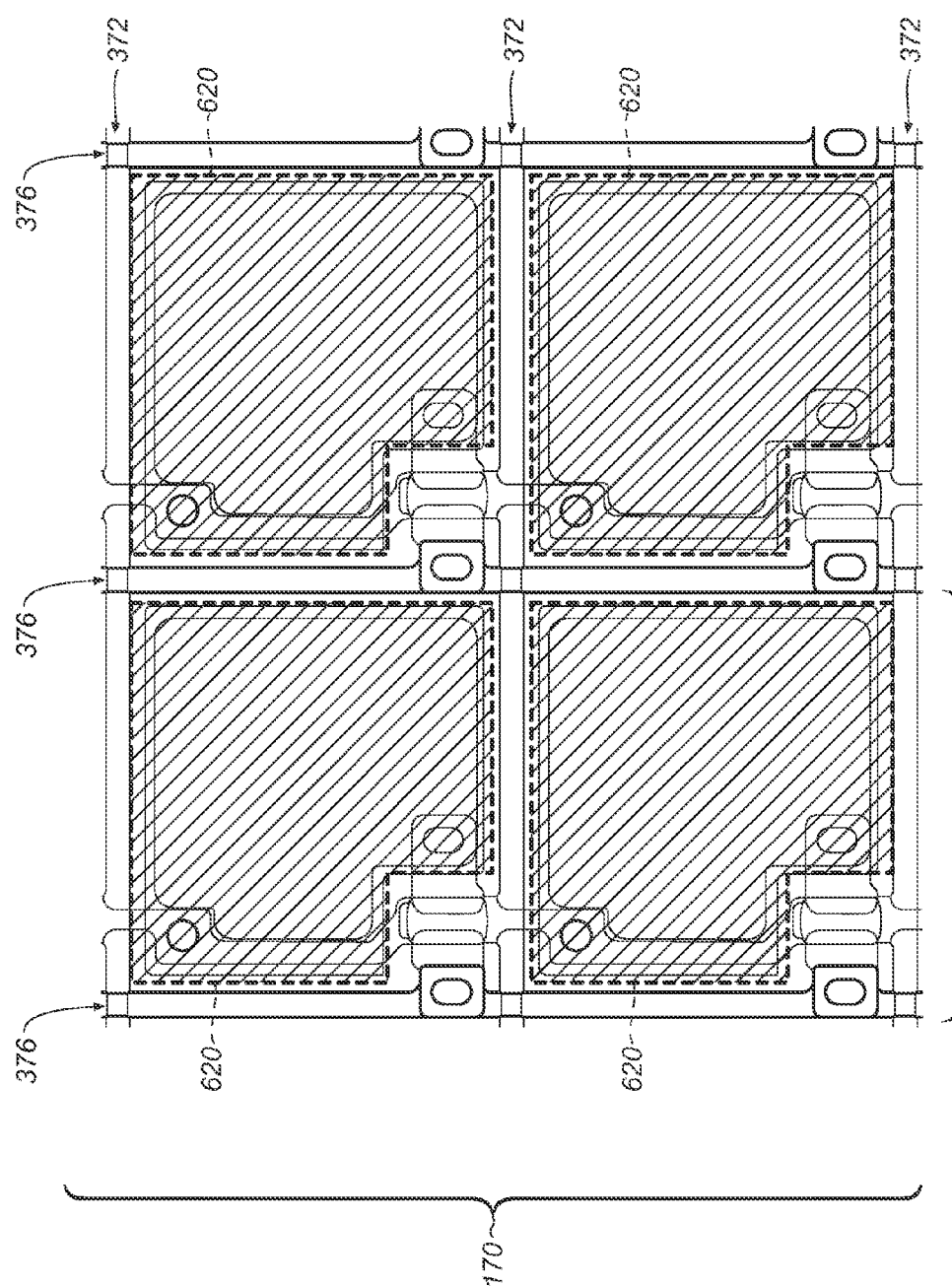
FIG. 26 is a diagram that shows a top-down view of a layout for a patterned anti-static coating shown in FIG. 25.

FIG. 25 is a diagram that shows a cross-section of another embodiment of a radiographic detector configured to include an imaging array with a patterned anti-static layer thereover. FIG. 26 is a diagram that shows a top-down view of a layout for a patterned anti-static coating shown in FIG. 25. As shown in FIG. 25, contact to a patterned anti-stat layer 620 embodiment on the imaging array 170 can be provided by a conductor or conductive anti-static coating 625 on the scintillator 180. The conductivity from the patterned anti-static layers 620 on the imaging array 170 can be electrically coupled the anti-static layer 625 on the scintillator 180, thereby providing a continuous sheet with low resistance to any pixel 100 in the imaging array 170 in comparison with embodiments shown FIG. 22 to FIG. 24. As a result, no connecting regions (e.g., 422, 522) are required in the anti-static layer 620 of the imaging array 170 itself, and a layout can be provided in which the anti-static layer 620 is only over the photosensor.

Figure 27:
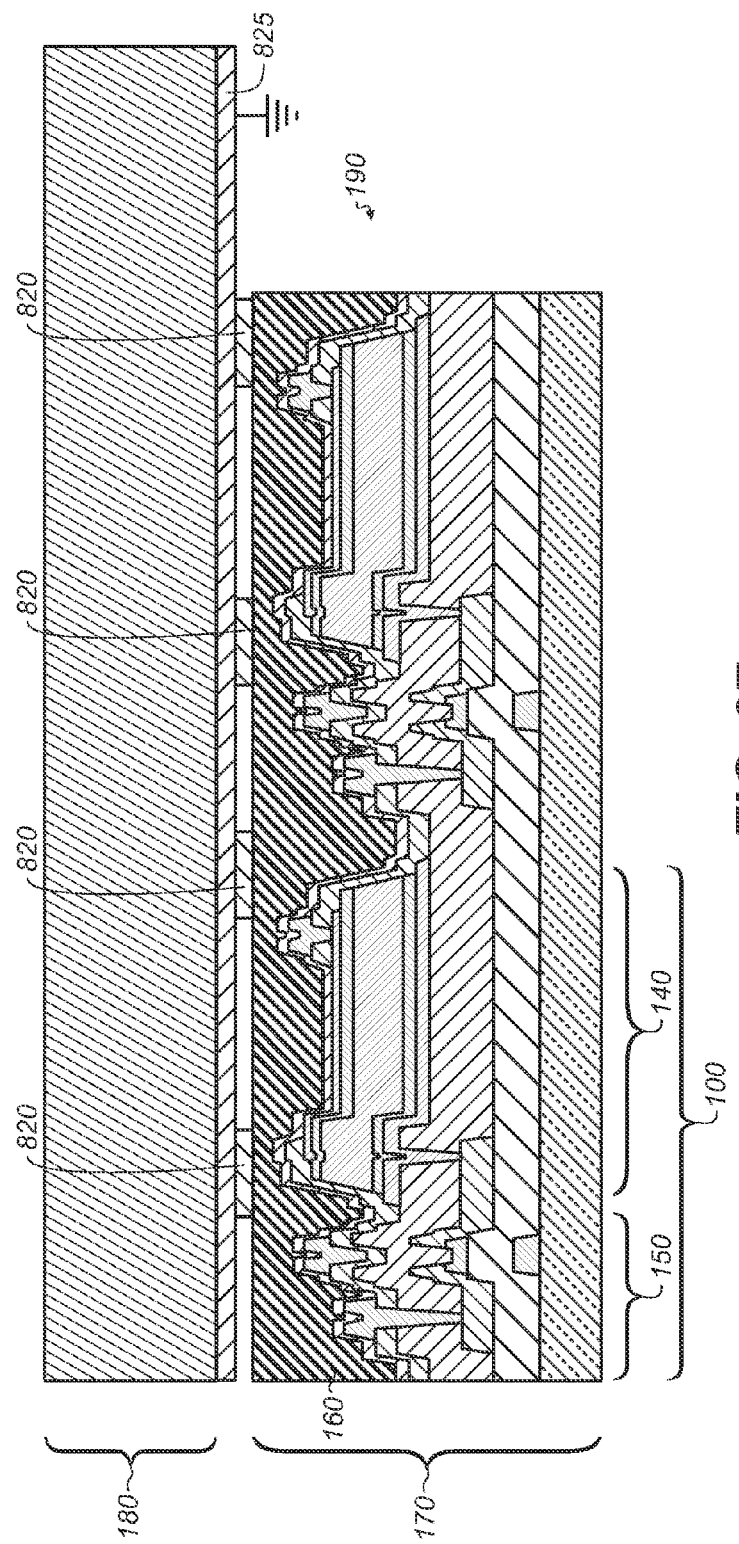
FIG. 27 is a diagram that shows a cross-section of another embodiment of a radiographic detector configured to include an imaging array with a patterned anti-static layer thereover.

FIG. 27 is a diagram that shows a cross-section of another embodiment of a radiographic detector configured to include an imaging array with a patterned anti-static layer thereover. FIG. 28 is a diagram that shows a top-down view of a layout for a patterned anti-static coating embodiment shown in FIG. 27. As shown in FIG. 27, contact to a patterned anti-stat layer 820 embodiment on the imaging array 170 can be provided by a conductor or anti-static coating 825 on the scintillator 180. As shown in FIGS. 27-28, the patterned anti-stat layer 820 embodiment on the imaging array 170 can cover the perimeter of the photodiode. Advantages for patterned anti-stat layer 820 embodiment can include the following. The photodiode anode can be a transparent electrode contacting to a bias line, and therefore the photodiode anode can be protected from all but very high static charge by the bias line ESD protection circuits. The sidewalls of the photodiode, however, are not covered and can be sensitive to static charge. Static charge in the proximity of the sidewall can cause increased leakage current, image lag and/or low-frequency (e.g., flicker) pixel noise. Thus, the patterned anti-stat layer 820 embodiment over just the perimeter area not protected by the transparent anode connection can allow increased light transmission to the photodiode and reduced diode capacitance.

Additional embodiments can implement interconnection schemes for the patterned anti-static layers of FIGS. 22-24. For such embodiments contact to the anti-static layer for a reference voltage can be provided by pads on the array substrate located at the perimeter of the imaging area and/or through the scintillator. For example in one embodiment, a patterned anti-static layer can be contacted by contact pads provided around the perimeter of the imaging area, as illustrated in FIG. 14.

For certain exemplary embodiments of patterned anti-static layers, the patterned anti-static layers can include a colorant material to block at least a portion of the light incident on the imaging array. In one embodiment, the anti-static layer 820 shown in FIG. 28 can contain a colorant material that can block at least a portion of the light incident on the imaging array 170. The colorant material or colorant can be spectrally selective, to block, for example, one or more spectral bands emitted from the scintillator 180 or blocking visible light to which the photosensor 140 or photodiode is sensitive (e.g., typically between 400 and 700 nm). Examples of colorant materials include pigments, dyes or particulate matter such as carbon particles or carbon fiber. Various advantages can be achieved by adding colorant to block light from the photodiode perimeter. Interface states at the amorphous silicon-silicon nitride surface on the sidewall can cause trapping or excessive trapping of photogenerated charge, which can result in image lag. By blocking light from the sidewall, the image lag can be reduced while the quantum efficiency is only slightly reduced.

Figure 29B:
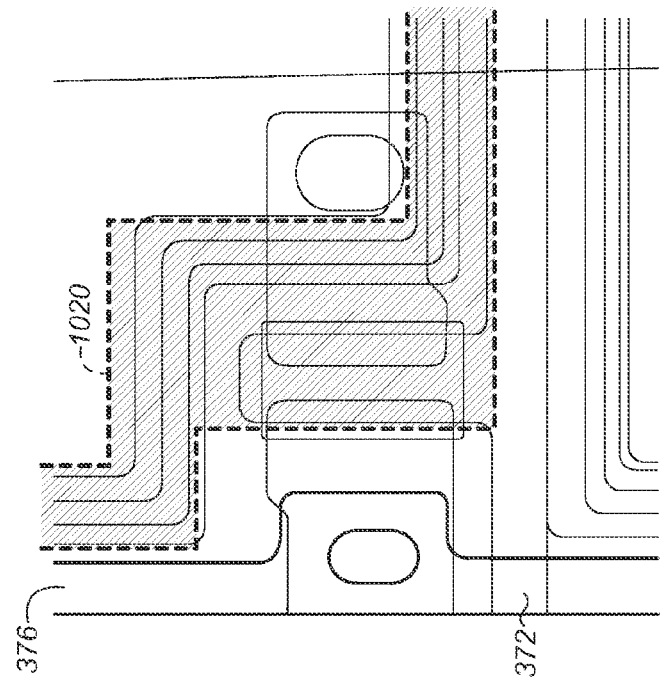
FIGS. 29A-29B are a diagram that shows a top-down view of a layout for a patterned anti-static coating where
Figure 29A:
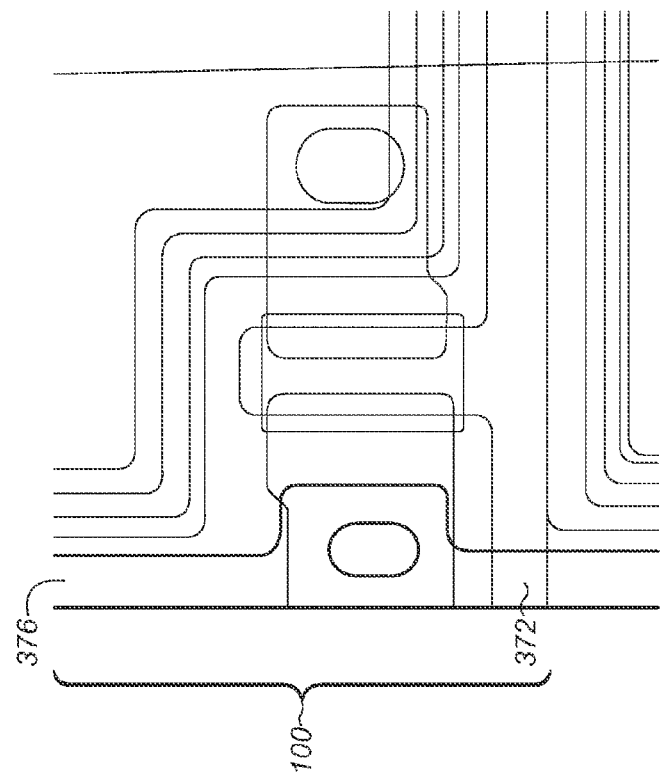

In another anti-static layer embodiment, the anti-static layer can include a colorant material and can extend over the readout circuitry in addition to the photodiode perimeter. In related art radiographic imaging arrays, a metal light shield is provided over the back of the switching TFT, for example as shown in FIG. 21. The light shield is required to reduce or prevent light absorption in the TFT (e.g., 150), which can cause an increase in leakage current and long-term TFT instability. However, the light shield can add capacitance to the TFT and the dataline, which can result in increased thermal noise. As shown in FIG. 29B, a pixel has an overlay indicating a layout of the anti-static coating pattern 1020 extending over the readout circuit and the same pixel without a metal light-shield is shown in FIG. 29A.

Additional alternate embodiments for electrical connection of anti-static layers can use conductive traces in the radiographic imaging array to provide a reference voltage (e.g., ground reference) to the anti-static layers. For example, electrical grounding for the anti-static layers 220, 320, 420, 520, 620, 820, 1020 can use (a) separate metal traces for anti-static connection within the array and vias between these metal traces and the anti-static layer and/or (b) provide a sparse matrix of connections to the anti-static layer in the imaging array positioned between a limited number of pixels (e.g., such as every 256 rows or 256 columns, at selected prescribed locations, aperiodic, etc.).

Exemplary embodiments of conductive traces can include high transparency to light emitted by the scintillator and an index of refraction corresponding to the imaging array/scintillator.

Alternate embodiments for electrical connection of anti-static layers can use physical contact(s) or electrical coupling provided through a conductive coating or an anti-static coating on the scintillator, preferably where the scintillator anti-static coating is attached or electrically connected to a reference voltage or ground connection.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value equal to or greater than zero and a maximum value equal to or less than 10, e.g., 1 to 5. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" or "and/or" with respect to a listing of items such as, for example, "A and B" or "A and/or B", means A alone, B alone, or A and B.

Further, in the discussion and claims herein, the term "on" used with respect to two materials, one "on" the other, means at least some contact between the materials, while "over" means the materials are in proximity or near each other, but possibly with one or more additional intervening materials such that contact is possible but not required. Neither "on" nor "over" implies any directionality as used herein. The term between as used herein with respect to two elements means that an element C that is "between" elements A and B is spatially located in at least one direction such that A is proximate to C and C is proximate to B or vice versa. The term "conformal" describes a coating material in which angles of the underlying material are preserved by the conformal material.

In accordance with one embodiment, there can be provided a projection radiographic imaging apparatus, that can include an insulating substrate; a radiographic imaging array formed over the insulating substrate, the radiographic imaging array comprising imaging pixels, each pixel including at least one readout element and one photosensor; a scintillator to convert first radiographic radiation of one or multiple wavelengths range to second different photoelectric radiation of one or multiple wavelengths range proximate to the radiographic imaging array; and a continuous anti-static layer disposed between the radiographic imaging array and the scintillator.

In accordance with one embodiment, there can be provided a method of manufacturing a radiographic detector imaging apparatus that can include forming an insulating substrate; forming a radiographic imaging array formed over a substrate, the imaging array including imaging pixels, each pixel comprising at least one readout element and one photosensor, where the photosensor is a polycrystalline photosensor or an amorphous photosensor; forming a scintillator to convert first radiographic radiation of one or multiple wavelengths range to second different photoelectric radiation of one or multiple wavelengths range proximate to the imaging array; and forming a continuous anti-static layer disposed between the radiographic imaging array and the scintillator.

In accordance with one embodiment, there can be provided a projection radiographic imaging apparatus, that can include an insulating substrate; a radiographic imaging array over the insulating substrate, the radiographic imaging array comprising imaging pixels, each pixel including at least one readout element and one photosensor; an insulating layer over a portion of the imaging pixels; a scintillator to convert first radiographic radiation of one or multiple wavelengths range to second different photoelectric radiation of one or multiple wavelengths range proximate to the radiographic imaging array; and an anti-static layer disposed between the insulating layer and the scintillator in which the anti-static layer is patterned in registration to the portion of the imaging pixels.

In accordance with one embodiment, there can be provided a method of manufacturing a radiographic detector imaging apparatus that can include forming an insulating substrate; forming a radiographic imaging array formed over the insulating substrate, the imaging array comprising imaging pixels, each pixel including at least one readout element and one photosensor, where the photosensor is a polycrystalline photosensor or an amorphous photosensor; forming a scintillator to convert first radiographic radiation of one or multiple wavelengths range to second different photoelectric radiation of one or multiple wavelengths range proximate to the imaging array; and forming a anti-static layer disposed between the radiographic imaging array and the scintillator, where the anti-static layer is patterned in registration to the imaging array.

In accordance with certain exemplary embodiments, the continuous or patterned anti-static layer is an anti-static coating of an organic material. In one embodiment, the continuous or patterned anti-static layer can be an anti-static coating comprising a nano-rods with an organic binder. In one embodiment, the continuous or patterned anti-static layer is an anti-static coating comprising a sub-atomic layer of transparent conductor. In one embodiment, the resistivity of the continuous or patterned anti-static layer is between $1\times10^4$ ohms per square and $1\times10^{10}$ ohms per square. In one embodiment, a thickness of the continuous or patterned anti-static layer is less than 10 microns. In one embodiment, the real part of the dielectric constant of the continuous or patterned anti-static layer is between 2.5 and 4. In one embodiment, the optical index of the continuous or patterned anti-static layer is between 1.5 and 2.5 or where the optical transmission of the continuous or patterned anti-static layer is greater than 90% between the wavelengths of 450 nm and 650 nm. One embodiment further comprises an organic insulating layer positioned between the array and the anti-static coating. In one embodiment, the organic insulating layer has a dielectric constant less than 3.0. In one embodiment, the continuous or patterned anti-static layer is connected to one or more conductive traces in the radiographic imaging array.

In one embodiment, the conductive traces are positioned external to the radiographic imaging array, and further comprising vias in insulating layers between the continuous or patterned anti-static layer and the conductive traces. In one embodiment, the conductive traces are positioned within one or more pixels of the radiographic imaging array, and further comprising vias in insulating layers between the continuous or patterned anti-static layer and the conductive traces at connection sites, where the continuous or patterned anti-static layer is connected to the conductive traces at the connection sites. In one embodiment, the conductive traces are positioned between one or more pixels of the radiographic imaging array, and further comprising vias in insulating layers between the continuous or patterned anti-static layer and the conductive traces at connection sites, where the continuous or patterned anti-static layer is connected to the conductive traces at the connection sites. In one embodiment, the conductive traces comprise one of the bias lines providing voltage to an element of the pixel or common photodiode bias lines, and further comprising vias in insulating layers between the continuous or patterned anti-static layer and the conductive traces at connection sites, where the continuous or patterned anti-static layer is connected to the conductive traces at the connection sites. In one embodiment, the conductive traces are separated by at least 16 rows or 16 columns of pixels, and where a number of connection sites comprising vias in insulating layers between the continuous or patterned anti-static layer and the conductive traces is less than 6% of the number of pixels in the radiographic imaging array.

In one embodiment, the anti-static layer is patterned in registration to the portion of the imaging pixels. In one embodiment, the patterned anti-static coating selectively covers the photosensor without substantially covering the readout element or a conductive trace including a data line. In one embodiment, the patterned anti-static coating selectively covers the photosensor and covers at least one of the dataline by less than 50% of the pixel dimension and the gateline by less than 50% of the pixel dimension. In one embodiment, the patterned anti-static layer contains a colorant. In one embodiment, the colorant comprises one or more of a pigment, a dye, a substantially opaque material, or is substantially opaque to light between 450 nm and 650 nm. In one embodiment, the patterned anti-static layer is configured to substantially cover the portion of the photodiode not covered by the anode. In one embodiment, the patterned anti-static layer is configured to substantially cover the channel region of the one or more transistors in the readout circuit.

In one embodiment, the first dielectric layer is substantially transparent to visible light with wavelength between 450 nm and 650 nm, and an average refractive index of the dielectric layer is between 1.4 and 1.8. In one embodiment, the first dielectric layer is substantially transparent to visible light with wavelength between 450 nm and 650 nm, and where the second dielectric layer is substantially opaque to visible light with wavelength between 450 nm and 650 nm. In one embodiment, a thickness of the first dielectric is less than one-half of the thickness of the second dielectric, or a thickness of the first dielectric is less than 10 microns. In one embodiment, a scintillator can be deposited on the imaging array, deposited by evaporation on the imaging array, attached to the imaging array, attached by thermal setting to the imaging array, attached by an adhesive to the imaging array, or pressed to the imaging array, where the scintillator is CsI deposited on the imaging array or where the scintillator is coated on the array, where the coated scintillator comprises an organic binder and phosphor particles.

In certain exemplary embodiments, digital radiographic imaging detectors can include thin-film elements such as but not limited to thin-film photosensors and thin-film transistors. Thin film circuits can be fabricated from deposited thin films on insulating substrates as known to one skilled in the art of radiographic imaging. Exemplary thin film circuits can include amorphous-silicon devices such as a-Si PIN diodes, schottky diodes, MIS photocapacitors, and be implemented using amorphous semiconductor materials or polycrystalline semiconductor materials such as silicon.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A projection radiographic imaging apparatus, comprising:

an insulating substrate;

an imaging array formed over the insulating substrate, the imaging array comprising imaging pixels, each pixel comprising at least one readout element and one photosensor;

a scintillator to convert first radiographic radiation of one or multiple wavelengths range to second different photoelectric radiation of one or multiple wavelengths range proximate to the imaging array;

a first dielectric layer formed between the scintillator and the imaging array, wherein the dielectric constant of the first dielectric layer is less than 3.0, and an anti-static layer disposed between the imaging array and the scintillator, where the anti-static layer is continuous or patterned in registration to a portion of the imaging pixels, where the continuous or patterned anti-static layer is connected to one or more conductive traces in the radiographic imaging array.

2. The radiographic imaging apparatus of claim 1, wherein a portion of the first dielectric layer that is disposed over a conductive line is thicker than a portion of the dielectric layer that is disposed over at least one of the photosensors, the conductive line comprising a data line or a bias line.

3. The radiographic imaging apparatus of claim 1, where the conductive traces are positioned (a) within one or more pixels of the radiographic imaging array, and wherein the imaging apparatus further comprises vias in insulating layers between the patterned anti-static layer and the conductive traces, or (b) between pixels of the radiographic imaging array, and wherein the imaging apparatus further comprises vias in insulating layers between the patterned anti-static layer and the conductive traces.

4. The radiographic imaging apparatus of claim 1, further comprising a second dielectric layer formed over at least a portion of the imaging array that does not include one of the photosensors.

5. The radiographic imaging apparatus of claim 4, where the dielectric constant of the first dielectric layer or the second dielectric layer is less than 2.8, and where the second dielectric layer contains colorants.

6. The radiographic imaging apparatus of claim 4, where a substantially opaque insulating layer is positioned between the scintillator and channel regions of one or more thin-film-transistors in the readout elements, where the substantially opaque insulating layer is positioned between the scintillator and sidewalls of mesa photosensors, where the substantially opaque insulating layer is positioned between the scintillator and one or more of data lines, bias lines and scan lines, or where the substantially opaque insulating layer is positioned between the scintillator and regions of the pixels substantially transparent to illumination from the scintillator.

7. The radiographic imaging apparatus of claim 4, wherein the anti-static layer or an adhesive layer is disposed between the first dielectric layer and the scintillator or between both the first dielectric layer and the second dielectric layer and the scintillator, where at least one of the anti-static layer or the adhesive layer are attached or coated on the scintillator before the scintillator is attached to the imaging array.

8. The radiographic imaging apparatus of claim 4, where the first dielectric layer or the second dielectric layer comprises an organic material, and where a dielectric constant of the scintillator is greater than 4.0, and comprising an anti-static layer disposed between the radiographic imaging array and the scintillator, where the anti-static layer is continuous or patterned in registration to a portion of the imaging pixels.

9. The radiographic imaging apparatus of claim 1, where the first dielectric layer is an adhesive layer with a dielectric constant less than 3.0.

10. The radiographic imaging apparatus of claim 1, further comprising an adhesive layer, where the adhesive layer comprises anti-static properties or anti-static material.

11. The radiographic imaging apparatus of claim 1, further comprising an adhesive layer, where a combined dielectric property of the adhesive layer and the first dielectric layer satisfy a prescribed dielectric requirement of an encapsulation of the imaging array.

12. The radiographic imaging apparatus of claim 1, where the conductive traces are separated by at least 16 rows or 16 columns of pixels, and where a number of vias in insulating layers between the patterned anti-static layer and the conductive traces is less than 6% of the number of pixels in the radiographic imaging array.

13. The radiographic imaging array of claim 1, where the patterned anti-static layer selectively covers the photosensor without substantially covering the readout element or the one or more conductive traces including a data line, and where the patterned anti-static layer contains a colorant.

14. The radiographic imaging apparatus of claim 1, wherein a number of connection sites comprising vias between the patterned anti-static layer and the conductive traces is less than 6% of a number of pixels in the imaging array.

15. A method of manufacturing a radiographic detector imaging apparatus comprising:
    forming an insulating substrate;
    forming an imaging array over the substrate, the imaging array comprising imaging pixels, each pixel comprising at least one readout element and one photosensor, where the photosensor is a polycrystalline photosensor or an amorphous photosensor;
    forming a scintillator over the imaging array to convert first radiographic radiation of one or multiple wavelengths range to second different photoelectric radiation of one or multiple wavelengths range proximate to the imaging array;
    forming a first insulating layer that comprises organic material between the scintillator and the imaging array, where a dielectric constant of the first insulating layer is less than 3.3, and
    forming a first anti-static layer between the imaging array and the scintillator, where the anti-static layer is continuous or patterned in registration to a portion of the imaging pixels, where the anti-static layer selectively covers the photosensors without substantially covering the readout elements or data lines.

16. The method of claim 15, further comprising incorporating a colorant into the anti-static layer.

17. The method of claim 15, further comprising forming a conductive trace in the radiographic imaging array and connecting the anti-static layer to the conductive trace.

18. The method of claim 17, wherein the step of forming the conductive trace in the radiographic imaging array comprises forming the conductive trace on the scintillator.

19. The method of claim 15, further comprising forming a grounded conductor layer or a grounded anti-static layer on a surface of the scintillator and electrically connecting the first anti-static layer thereto.

* * * * *

UNITED STATES PATENT AND TRADEMARK OFFICE
CERTIFICATE OF CORRECTION

PATENT NO. : 8,866,099 B2  
APPLICATION NO. : 13/798244  
DATED : October 21, 2014  
INVENTOR(S) : Timothy J. Tredwell et al.

Page 1 of 1

It is certified that error appears in the above-identified patent and that said Letters Patent is hereby corrected as shown below:

Title Page, item (71) Applicants and (72) Inventors     Inventors should read --Timothy J. Tredwell, Fairport, NY (US); Gregory N. Heiler, Hilton, NY (US); Seshadri Jagannathan, Rochester, NY (US)--

Signed and Sealed this  
Seventh Day of April, 2015

Michelle K. Lee  
*Director of the United States Patent and Trademark Office*